(12) United States Patent
Misener et al.

(10) Patent No.: US 11,666,909 B2
(45) Date of Patent: Jun. 6, 2023

(54) HEMATOLOGY TEST SLIDE

(71) Applicant: IDEXX Laboratories, Inc., Westbrook, ME (US)

(72) Inventors: Garland Christian Misener, Portland, ME (US); Richard Ellis Holt, Old Orchard Beach, ME (US); Keith Nassif, Saco, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 17/469,215

(22) Filed: Sep. 8, 2021

(65) Prior Publication Data

US 2021/0402400 A1   Dec. 30, 2021

Related U.S. Application Data

(62) Division of application No. 15/769,665, filed as application No. PCT/US2016/058157 on Oct. 21, 2016, now Pat. No. 11,141,725.
(Continued)

(51) Int. Cl.
*B01L 3/00*  (2006.01)
*G02B 21/34* (2006.01)
(Continued)

(52) U.S. Cl.
CPC ... *B01L 3/502715* (2013.01); *B01L 3/502707* (2013.01); *B01L 9/52* (2013.01);
(Continued)

(58) Field of Classification Search
CPC ......... B01L 3/502715; B01L 3/502707; B01L 9/52; B01L 2300/0609; B01L 2300/0822;
(Continued)

(56) References Cited

U.S. PATENT DOCUMENTS 3,961,346 A   6/1976   White .......................... 356/244
4,637,693 A   1/1987   Mitchell ....................... 359/398
(Continued)

FOREIGN PATENT DOCUMENTS

DE   3830721 A1   3/1990   ................ B01L 3/00
EP   0437408 A2   7/1991   ................ B01L 3/00
(Continued)

OTHER PUBLICATIONS

Morel, et al., "*Microfluidic Stickers for Cell- and Tissue-Based Assays in Microchannels*", DOI: 10.1039/b819090a, Dec. 5, 2008, the whole document. Abstract and full text available at: https://www.researchgate.net/publication/24208380_Microfluidic_stickers_for_cell-_and_tissue-based_assays_in_microchannels (last accessed on Dec. 27, 2021) (copy not enclosed).
(Continued)

*Primary Examiner* — Dennis White
(74) *Attorney, Agent, or Firm* — Bodner & O'Rourke, LLP; Gerald T. Bodner; Christian P. Bodner

(57) ABSTRACT

A hematology test slide has the same or similar dimensions as a chemical reagent test slide and an immunoassay test slide so that it may be used with these other slides on a single clinical instrument. The hematology slide includes, in order from top to bottom, a slide housing having a top housing member, a top cover slip, a U-shaped, transfer tape spacer, a bottom cover slip, a base gasket and a base plate. The U-shaped spacer has a curved end portion which defines a sample deposit area, where a blood sample is pipetted thereon, and a pair of straight, parallel, spaced apart legs extending from the curved end portion. The legs define a read area. A blood sample deposited on the hematology slide at the sample deposit area will flow by capillary action to the read area, where optical measurements are made on the sample.

24 Claims, 22 Drawing Sheets

Related U.S. Application Data

(60) Provisional application No. 62/246,325, filed on Oct. 26, 2015.

(51) Int. Cl.
*B01L 9/00* (2006.01)
*G01N 33/487* (2006.01)

(52) U.S. Cl.
CPC ...... *G02B 21/34* (2013.01); *B01L 2300/0609* (2013.01); *B01L 2300/0822* (2013.01); *B01L 2300/168* (2013.01); *B01L 2400/0406* (2013.01); *G01N 33/4875* (2013.01)

(58) Field of Classification Search
CPC ....... B01L 2300/168; B01L 2400/0406; G02B 21/34; G01N 33/4875
See application file for complete search history.

(56) References Cited

U.S. PATENT DOCUMENTS

| | | | |
|---|---|---|---|
| 4,790,640 A | 12/1988 | Nason | 359/396 |
| 5,089,229 A | 2/1992 | Heidt et al. | 422/64 |
| 5,348,859 A | 9/1994 | Brunhouse et al. | 435/7.24 |
| 7,026,131 B2 | 4/2006 | Hurt et al. | 435/7.25 |
| D530,826 S | 10/2006 | Rich et al. | D24/225 |
| 7,273,591 B2 | 9/2007 | Sellers et al. | 422/563 |
| 7,588,733 B2 | 9/2009 | Rich et al. | 422/561 |
| 8,310,658 B2 | 11/2012 | Wardlaw et al. | 356/39 |
| 8,361,799 B2 | 1/2013 | Levine et al. | 436/70 |
| 8,440,425 B2 | 5/2013 | Jaekel | 435/40.5 |
| 8,837,803 B2 | 9/2014 | Wang et al. | 382/134 |
| 9,483,686 B2 | 11/2016 | Yu et al. | |
| 9,797,916 B2 | 10/2017 | Connolly et al. | |
| 9,933,428 B2 | 4/2018 | Chan et al. | |
| 10,082,660 B2 | 9/2018 | Stoecker et al. | |
| 2005/0221283 A1 | 10/2005 | Mahant et al. | 435/5 |
| 2007/0087442 A1 | 4/2007 | Wardlaw | 436/165 |
| 2007/0243117 A1 | 10/2007 | Wardlaw | 422/255 |
| 2010/0254854 A1 | 10/2010 | Rich et al. | 422/64 |
| 2011/0034348 A1 | 2/2011 | Deutsch et al. | 506/14 |
| 2011/0312531 A1 | 12/2011 | Jacobs et al. | 506/9 |
| 2014/0308661 A1 | 10/2014 | Holmes et al. | 435/6.1 |
| 2014/0315216 A1 | 10/2014 | Chan et al. | 435/7.4 |
| 2015/0017709 A1 | 1/2015 | Brown et al. | 435/283.1 |
| 2015/0031051 A1 | 1/2015 | Mohan et al. | 435/7.24 |
| 2015/0031116 A1 | 1/2015 | Quake et al. | 435/283.1 |

FOREIGN PATENT DOCUMENTS

| | | | | |
|---|---|---|---|---|
| EP | 2802869 | | 11/2014 | G01N 33/543 |
| EP | 2896458 A1 | | 7/2015 | B01L 3/00 |
| WO | WO2014165373 A1 | | 10/2014 | B01L 3/00 |

OTHER PUBLICATIONS

Notification of Transmittal of the International Search Report and the Written Opinion of the International Searching Authority, or the Declaration, dated Jan. 10, 2017, which was issued by the International Searching Authority of WIPO in Applicant's corresponding international PCT application having Serial No. PCT/US2016/058157, filed on Oct. 21, 2016.

Written Opinion of the International Searching Authority, dated Jan. 10, 2017, which was issued by the International Searching Authority of WIPO in Applicant's corresponding international PCT application having Serial No. PCT/US2016/058157, filed on Oct. 21, 2016.

International Search Report, dated Jan. 10, 2017, which was issued by the International Searching Authority of WIPO in Applicant's corresponding international PCT application having Serial No. PCT/US2016/058157, filed on Oct. 21, 2016.

Supplementary European Search Report and Annex to the European Search Report, in English, dated Feb. 14, 2019, issued from the European Patent Office for Applicant's corresponding European Patent Application No. EP16860550.9, filed on May 25, 2018.

HEMATOLOGY TEST SLIDE

CROSS-REFERENCE TO RELATED APPLICATIONS

This application is a divisional of co-pending U.S. patent application Ser. No. 15/769,665, filed on Apr. 19, 2018, and entitled "Hematology Test Slide", which claims the benefit of priority, under 35 U.S.C. 371, to international PCT Application Serial No. PCT/US2016/058157, filed on Oct. 21, 2016, and, under 35 U.S.C. 119 and/or 35 U.S.C. 120, to U.S. Provisional Application Ser. No. 62/246,325, filed on Oct. 26, 2015, and entitled "Hematology Test Slide", the disclosure of each of which is incorporated herein by reference and on which priority is hereby claimed.

BACKGROUND OF THE INVENTION

Field of the Invention

The present invention generally relates to devices for performing hematology measurements on a blood sample in an automated clinical instrument for human and veterinary applications, and more particularly relates to a test slide for performing such hematology measurements.

Description of the Prior Art

Automated clinical instruments and chemistry analyzers for performing chemistry, electrolyte and immunoassay tests on a single whole blood sample are well known in the art. Such instruments and analyzers include the VetTest™ analyzer, disclosed in U.S. Pat. No. 5,089,229 (Heidt, et al.); the Catalyst DX™ analyzer, disclosed in U.S. Patent Application Publication No. 2010/0254854 (Rich, et al.); and the Catalyst One™ analyzer disclosed in U.S. patent application Ser. No. 14/592,282, filed on Jan. 8, 2015 and entitled "Chemical Analyzer" (the '282 application), the disclosure of each of which is incorporated herein by reference. Each of the aforementioned instruments is manufactured and sold by IDEXX Laboratories, Inc. of Westbrook, Me., United States, and each of the aforementioned patents and U.S. applications is assigned of record to or owned by IDEXX Laboratories, Inc.

These analyzers utilize dry chemical reagent test slides, having a film surrounded by a frame, such as the rectangular slides disclosed in the aforementioned Heidt, et al. patent and in U.S. Pat. No. 7,273,591 (Sellers, et al.), or for example, the trapezoidally-shaped reagent test slide disclosed in the aforementioned Rich, et al. published U.S. application and the Sellers, et al. patent (see FIG. 15 thereof), and in U.S. Pat. Nos. D530,826 (Rich, et al.) and U.S. Pat. No. 7,588,733 (Rich, et al.), each of which is assigned of record to IDEXX Laboratories, Inc., the disclosure of each of which is incorporated herein by reference, to analyze a blood or fluid sample deposited thereon. The test slides are loaded onto a transport mechanism of the analytical instrument, which sequentially moves each slide under a sample metering device, which deposits a fluid sample on the slide, and then above an optics module, incorporating a reflectometer or fluorometer, or both, the optics module having a sapphire window through which light is transmitted to illuminate a test slide positioned over it and through which reflected or fluoresced light from the slide is received. More specifically, the sample deposited on the slide reacts with the chemical reagent on the film, and the reflectance or fluorescence of the slides is then measured by the chemical analyzer to determine the concentration of a compound or substance found in the sample, such as calcium (Ca), aspartate transaminase (AST) or glucose (Glu), which could be an indication of a condition or a disease. Only small aliquots of sample need to be deposited on the slides for detection of the analyte concentrations. Such tests are performed by the analyzer concurrently and in an automated and efficient fashion.

Immunoassay test slides have also been developed by IDEXX Laboratories, Inc. to perform assays and tests thereon for detecting the presence or quantity of an analyte (e.g., an antigen or antibody, and the like). Such test slides are designed generally to conform to the same or similar dimensions of the chemical reagent test slides described earlier so that they are adapted to be used in one or more of the aforementioned dry chemistry analytical instruments, along with the chemical reagent test slides. Just like the chemical reagent test slides, the immunoassay test slides are moved by the transport mechanism of the analytical instrument under a sample metering device, which deposits a fluid sample on the slide, and then above a reflectometer or fluorometer, where the presence or quantity of a specific analyte of interest in the fluid sample may be determined from reflectance or fluorescence measurements performed on the slide. An example of such an immunoassay test slide is disclosed in U.S. Patent Application Publication No. 2014/0315216 (Chan, et al.), the disclosure of which is incorporated herein by reference. The aforementioned Chan, et al. published U.S. application is also assigned of record to IDEXX Laboratories, Inc.

Hematology tests on a blood sample are often performed manually or in a non-automated fashion. These tests include, for example, red blood cell (RBC) count, white blood cell (WBC) count, WBC differential (typically, three-, four-, or five-part), platelet (PLT) count, hemoglobin concentration (Hb or, also, HGB), mean red blood cells' corpuscular volume (MCV), and others. From such measurements, the mean corpuscular hemoglobin concentration (MCHC), hematocrit (HCT) and the mean corpuscular hemoglobin (MCH) mass may be calculated.

It would be advantageous if such hematology tests could be performed on the same dry chemistry analytical instruments that perform one or more clinical chemistry, electrolyte and immunoassay tests on similarly-shaped test slides that are compatible with such instruments.

OBJECTS AND SUMMARY OF THE INVENTION

It is an object of the present invention to provide a hematology test slide formed in accordance with the present invention which may be used in a dry chemistry analytical instrument for human and veterinary applications.

It is another object of the present invention to provide a method for conducting hematology measurements in a dry chemistry analytical instrument using the hematology test slide of the present invention.

In one form, a hematology test slide constructed in accordance with the present invention includes a top cover slip, preferably of glass, a bottom cover slip, also preferably of glass and situated below the top cover slip, and a spacer interposed between the top and bottom cover slips. The spacer serves several functions, one of which is to maintain a predetermined and accurate spacing between the top cover slip and the bottom cover slip. Together, the top and bottom cover slips define between them a cell for receiving an aliquot of blood sample. The spacer also provides a barrier for pipetted sample, ensuring that it flows into the cell defined by the cover slips and the spacer. For this reason, the spacer is preferably U-shaped, meaning that it has a closed end portion that may be curved (or straight) and an open end portion defined by parallel, straight, spaced apart legs extending from the closed end portion.

The top cover slip preferably does not cover the entire U-shaped spacer. Rather, only the parallel, straight, spaced apart legs, or portions thereof, are covered by the top cover slip; the curved end portion of the spacer preferably remains uncovered by the top cover slip so that a blood or fluid sample may be deposited from above the slide into the region or area defined inside the closed end portion. Such a blood sample, deposited in the area of the closed end portion of the spacer, will flow by capillary action between the top and bottom cover slips into the adjacent region or area defined by and between the parallel, straight legs of the spacer. Here, in this adjacent area, optical measurements are performed on the blood sample by, for example, a reflectometer or fluorometer or, preferably, a digital imaging camera, from below the bottom cover slip.

In a more preferred form of the hematology test slide of the present invention, the top and bottom cover slips, and the U-shaped spacer therebetween, may be received within protective slide housing. More specifically, the slide housing includes a top plate-like member situated above the top cover slip and having a square or rectangular recess formed in the underside of the member, the recess being dimensioned to receive therein the top and bottom cover slips and the spacer. The top housing member includes an opening formed through its thickness, which opening is in alignment with the sample deposit area defined by the closed end portion of the spacer (which is not covered by the top cover slip). An adhesive base gasket (for example, a double-sided tape) is placed between the underside of the bottom cover slip and a base plate. The base plate, forming part of the slide housing, is affixed by the adhesive base gasket to the top housing member in alignment with the recess, with the edges of the base plate adhering to a recessed lip surrounding the recess and formed in the underside of the top housing member by the adhesive base gasket. The base plate also preferably includes an opening formed through its thickness which is situated in alignment with the area defined between the straight leg portions of the U-shaped spacer where optical measurements are performed on the blood sample.

The base plate need not lie flush with the underside surface of the top housing member. Rather, it is more important that the base plate and the bottom cover slip that is supported by the base plate are disposed in parallel with the sapphire window of the optics module when the hematology slide is positioned over the window. The top housing member is used primarily for the protection of the interior components of the slide and may be slightly angled from the base plate mounted thereon; it is the base plate which insures that the optical axis of the optics module is perpendicular to the plane in which the bottom cover slip resides to effect a full and complete focusing of the area of the slide where optical measurements are performed.

The spacer is also preferably formed from a double-sided adhesive tape to hold the top and bottom slips together. The open end of the U-shaped spacer allows excess blood sample to flow into a well defined by the two cover slips but situated outside the read region or area reserved for imaging, reflectance, fluorescence and other optical measurements. The particular shape of the spacer, with its open end, will accommodate variations in the volume of blood or fluid sample deposited on the hematology test slide.

The outer dimensions of the hematology test slide of the present invention are preferably the same as or similar to those of a chemical reagent test slide or an immunoassay test slide, such as described previously herein, so that all three types of slides may be used on the same clinical instrument. In such a clinical instrument, multiple test slides are simultaneously moved along a circular path beneath a sample metering device and above a reflectometer or fluorometer, or other optics module, by a transport mechanism. In a preferred form of the hematology test slide, the opening formed through the top housing member through which an aliquot of blood or fluid sample is pipetted into the sample deposit area of the slide, and the opening formed in the base plate which is in alignment with the optical read region or area of the slide may be offset laterally from each other by a predetermined distance. The offset permits the optical read region to encompass a volume defined by the field of view of the optics module and the thickness of the spacer and, furthermore, permits some uncertainty in the volume of the fluid sample deposited. Like the chemical reagent test slide and the immunoassay test slide described previously, the housing of the hematology slide preferably has an overall trapezoidal shape.

In another preferred form of the hematology test slide of the present invention, the top housing member, or portions thereof situated above the optical read area, may be opaque to act as a "backdrop" for the imaged area, which may enhance white blood cell (WBC) imaging, in particular, and perhaps other imaging, as well.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
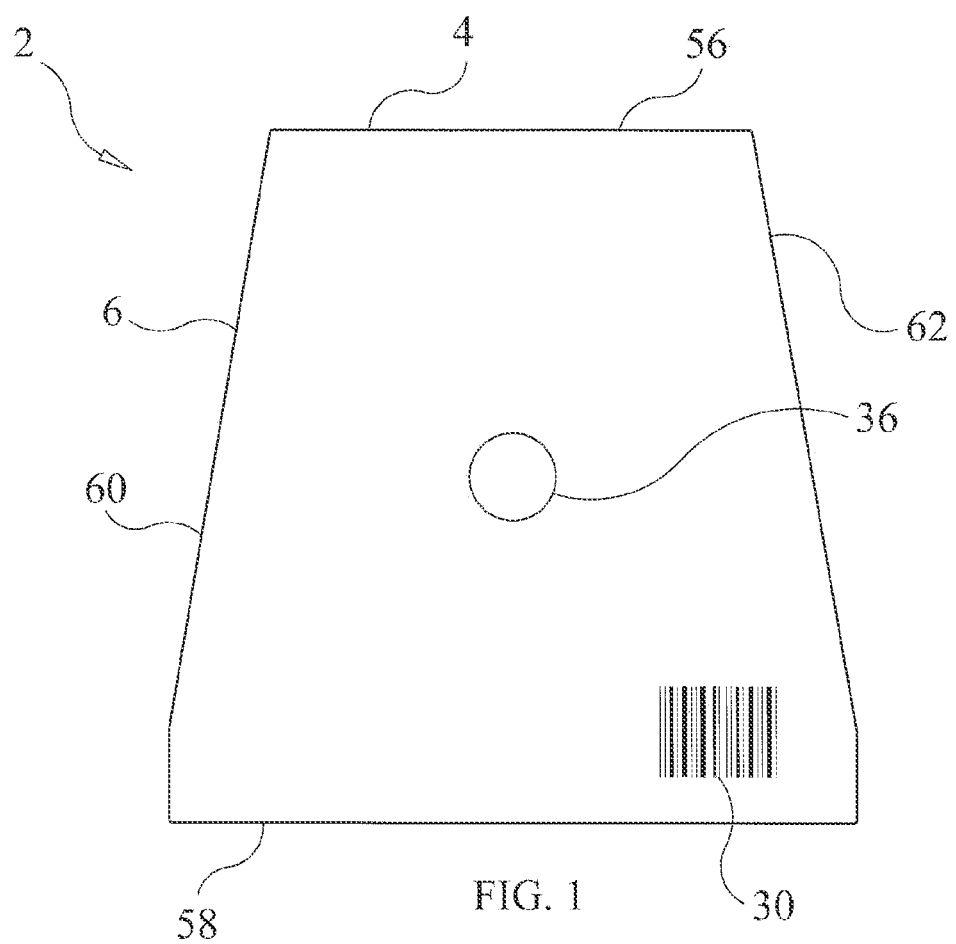
FIG. 1 is a top plan view of a hematology test slide formed in accordance with the present invention.

A preferred form of a hematology test slide 2, constructed in accordance with the present invention, is shown in FIGS. 1-21 of the drawings. In order of sequence, from top to bottom, the hematology test slide 2 preferably includes a slide housing 4 having a top housing member 6, a top cover slip 8, an adhesive spacer 10, which is preferably in the form of a double-sided adhesive tape, a bottom cover slip 12, a base gasket 14, which is also preferably in the form of a double-sided adhesive tape, and a base plate 16, which defines the lower portion of the slide housing 4. The slide housing 4 preferably has a generally trapezoidal shape, although it may take on other forms, such as square or rectangular, for example. The dimensions of the slide housing 4, in width, length and thickness, are chosen to be the same as or similar to those of the chemical reagent test slide and the immunoassay test slide disclosed in the aforementioned patents and published U.S. applications so that all three test slides, that is, reagent test slides, immunoassay test slides and the hematology test slides of the present invention, may be used and are compatible with the same dry chemistry analytical instrument and so that the instrument can run clinical chemistry, electrolyte, immunoassay and hematology tests on a single whole blood sample using the same instrument.

Preferably, the top cover slip 8 and the bottom cover slip 12 each are rectangular or square in shape, with the top cover slip 8 being smaller than the bottom cover slip 12. Each cover slip 8, 12 is preferably No. 1.5 in thickness, which means that they are typically about 170 microns to about 190 microns thick, but slip material of No. 1.5H in thickness may be used to achieve even higher resolution, which means that the top and bottom cover slips 8, 12 would then typically be about 170 microns to about 180 microns thick. The top and bottom cover slips 8, 12 are preferably formed from glass, although it is envisioned to be within the scope of the present invention to form the cover slips 8, 12 from another material that is preferably hydrophilic and can be molded to similar optical quality characteristics as cover slip glass. The bottom cover slip 12 must also be optically transparent. The top cover slip 8 resides over at least a portion of the bottom cover slip 12, leaving an adjacent portion 18 of the bottom cover slip 12 uncovered.

A spacer 10, which is preferably U-shaped, is interposed between the bottom cover slip 12 and the top cover slip 8. The spacer 10 includes a closed end portion 20 having a curved or straight transverse section, and a pair of parallel, straight, spaced apart legs 22 extending outwardly from the closed end portion 20. The spacer 10 may take on forms other than being U-shaped, as long as it defines a closed end portion 20 and open end portion 28 and does not entirely encircle a blood sample deposited on the test slide 2. Preferably, the spacer 10 is a double-sided adhesive tape, which adheres the top cover slip 8 to the bottom cover slip 12. Even more preferably, the spacer 10 is a transfer tape manufactured by 3M Company of St. Paul, Minn. or Adhesives Research, Inc. of Glen Rock, Pa. Together, the top and bottom cover slips 8, 12, held in place by the adhesive spacer 10, define between them a cell for receiving an aliquot of a blood sample. The "blood sample" is preferably treated, as needed, by one or more of dilution, addition of an RBC lysing agent, or a cell-staining reagent.

The adhesive spacer 10 serves several functions. First, the spacer 10 defines the thickness or depth of the cell for holding the blood sample. Second, the spacer 10, preferably being a double-sided adhesive transfer tape, adheres together the top and bottom cover slips 8, 12, which define the blood sample holding cell between them. Third, the spacer 10 provides a "moat" or region (hereinafter referred to as the "sample deposit area" 24) into which the sample is pipetted. The sample deposit area 24 is defined by the closed end portion 20 of the spacer 10.

The closed end portion 20 of the spacer 10 remains uncovered by the top cover slip 8 so that a blood or fluid sample may be deposited from above the slide 2 by a sample metering device or pipette into the sample deposit area 24 defined inside the closed end portion 20. Such a blood sample, deposited in the sample deposit area 24 of the closed end portion 20 of the spacer 10, will flow by capillary action between the top and bottom cover slips 8, 12 into the adjacent region (hereinafter referred to as the "optical read area" 26) defined by and between the parallel, straight legs 22 of the spacer 10. Here, in this adjacent optical read area 26, the optical measurements are performed on the blood sample by, for example, a reflectometer or fluorometer, or a digital imaging camera, from below the bottom cover slip 12. Stated another way, once the sample is deposited in the sample deposit area 24, it begins flowing towards the optical read area 26. The deposited sample droplet expands until it touches the interface between the top and bottom cover slips 8, 12, and then flows into the optical read area 26 and stops once the fluid forces balance.

An important reason for having the spacer 10 formed in a "U" shape, with a closed end portion 20 and with an open end 28 at the far end of the parallel, straight legged portion 22 that extends from the closed end portion 20, is because the volume of sample required to fill only the optical read area 26 is difficult to deposit precisely onto the slide. Typically, there may be an error of as the order of ±one microliter. And so, one of the features of the hematology slide 2 of the present invention is to provide a structure which can handle an over-volume of fluid sample deposited onto the slide 2. This feature is accomplished by having the sample flow from the sample deposit area 24 of the closed end portion 20 of the spacer 10 into the optical read area 26 defined between the parallel, straight legs 22 of the spacer 10 such that the sample fills the optical read area 26. If the volume of the blood sample deposited onto the slide 2 is sufficiently large, then the blood sample keeps flowing by capillary action out of the open end 28 defined by the parallel, straight legs 22 of the spacer 10 and fills an area beyond the open end 28 of the spacer 10 between the two cover slips 8, 12 which defines an overflow well. The flow of fluid sample will stop, and then an optical image, or a reflectance or fluorescence measurement, may be taken in the optical read area 26 of the cell between the straight legs 22 of the spacer 10. Extra fluid sample flows out of the open end 28 of the spacer 10, and can fill the entire volume between the two cover slips 8, 12.

As mentioned previously, the spacer 10 sets the thickness or depth of the viewing cell containing the blood sample. Preferably, the spacer 10 is between about twenty-five (25) microns and about two hundred and fifty (250) microns in thickness. The thickness of the spacer 10, especially when a transfer tape is used for the spacer, can be very accurately controlled or measured and, consequently, the volume of the viewing cell, at the optical read area 26, may be determined. Accurate volumes are crucial because hematology cell counts are reported per microliter.

A very thin spacer 10 may be used for conducting red blood cell (RBC) and platelet (PLT) counts, the spacer 10 having a thickness of between about three (3) microns and about five (5) microns, or about ten (10) microns and about fifty (50) microns, and preferably about 30 microns. Alternatively, for white blood cell (WBC) counts, the thickness of the spacer 10, which defines the depth of the cell between the cover slips 8, 12, may be larger. For example, in order to increase the counts, especially of monocytes, eosinophils or, possibly, basophils, in a WBC differential, the depth of the cell (and thus the thickness of the spacer 10) may be between about fifty (50) microns and about two hundred and fifty (250) microns, and is preferably about 50 microns to about 150 microns. Nevertheless, a range of about twenty-five (25) microns to about fifty (50) microns for the depth of the viewing cell defined between the top and bottom cover slips 8, 12, and thus the thickness of the spacer 10, is preferred if it is desired to have hematology slides with the same structure used for all three measurements (RBC count, platelet count and WBC count).

The exact depth of the viewing cell may be measured by a laser displacement meter, such as Model No. LT-9010M manufactured by Keyence Corporation of Osaka, Japan. It may be preferred to measure each assembly of top and bottom cover slips 8, 12 and spacer 10 in order to achieve needed volume accuracy within approximately one percent. But, if within-lot consistency is adequate, then it may be satisfactory to only measure the volume of these assemblies sampled from the lot. In the case where each assembly is measured individually for its cell depth, the volume information may be encoded on a machine-readable data code 30 located on the exposed upper surface of the top housing member 6. If the cell volume of sample assemblies from a lot is measured, that information could be provided with other slide lot information on the container of the lot of slides or, as mentioned previously, printed on each slide 2 of the lot.

The top cover slip 8 and the bottom cover slip 12, joined together by the spacer 10 interposed between them, is received in a recess 32 formed in the bottom surface 34 of the top member 6 of the slide housing 4. Preferably, the cover slips 8, 12 do not touch the slide housing 4. The recess 32 is preferably dimensioned in depth, width and length to fully receive the top and bottom cover slips 8, 12 and the spacer 10 therebetween.

The top housing member 6 includes an opening 36 formed through the thickness thereof, which opening 36 is situated in alignment with the sample deposit area 24 defined by the curved end portion 20 of the spacer 10 so that a blood or fluid sample may be deposited on the sample deposit area 24 through the opening 36 in the top housing member 6. This opening 36 may be rather small, that is, about two (2) millimeters to about five (5) millimeters, and preferably about three (3) millimeters, in diameter, which is sufficient to receive a blood or fluid sample deposited on the slide 2 by a pipette of a sample metering device of the automated clinical instrument, such as those described in the aforementioned patents and U.S. applications. By making the opening 36 in the top housing member 6 rather small, evaporation of the sample deposited on the slide 2 is minimized, and the rather delicate and breakable glass cover slips 8, 12 remain protected by the slide housing 4.

More specifically, the housing 4 provides several advantages for the hematology slide 2. First, it provides a barrier between the glass components (i.e., the top and bottom cover slips 8, 12) and the user and analyzer. The slide housing 4 provides a measure of safety because, with the cover slips 8, 12 being preferably made of glass and very thin and with the slide 2 carrying a blood sample, it is preferred to insure that the user is not able to touch the slide 2 without a protective housing. If no protective housing were provided, the user may cut himself with animal or human blood if he broke the very thin cover slips 8, 12 when handling the slide 2. The very thin cover slips 8, 12 would also be too delicate for a clinical analyzer to handle in an automated fashion.

Second, the slide housing 4 provides a containment of the sample. The blood sample deposited on the slide 2 is essentially contained within the slide 2 and the protective housing 4, even if the maximum expected volume of blood sample is pipetted onto the slide 2. The cover slips 8, 12 and cell defined between them is, effectively, encapsulated by the slide housing 4 so that the hematology slide 2 may be disposed of in the same manner as that of the chemical reagent test slides and immunoassay test slides.

Third, the slide housing 4 provides an added high-humidity environment surrounding the blood or fluid sample. Water vapor from any evaporated sample will increase the relative humidity within the pipetting opening 36 formed in the top housing member 6, slowing evaporation of the sample from this region 24. Thus, evaporation from within the slide 2 is minimized not only through the use of evaporation caps on the chemistry analyzer which are placed over the pipetting opening 36 formed in the top housing member 6 of the slide 2, but also by the slide itself. Minimization of sample evaporation is important to the functioning of slide 2 because bubbles or air gaps must not form in or influence the read area, else optically measured parameters be inaccurate.

Fourth, the top housing member 6 of the slide housing 4 may be clear or may be formed from a substantially opaque material, including being colored white or black. This opaque material acts as a backdrop for enhanced imaging, especially for white blood cell (WBC) imaging. Since the reflectometer or fluorometer, or optical imaging camera, of the analyzer is situated below the slide 2 to shine light into the optical read area 26 on the slide 2, the opaque top housing member 6 provides a backdrop to any imaging of the slide 2 to achieve better resolution of what is imaged. An opaque backdrop can highlight the cell shapes, making the cells easier to visualize and identify as being, for example, monocytes, lymphocytes or granulocytes. This is especially true if the slide 2 is illuminated at a high backscatter angle, such as about 150 degrees. Counting and identification of different cell types by dark field, backscattering illumination apparently may be optimized at angles between about 120 and about 180 degrees, where the latter occurs with the scattering source in-line with the imaging optics' objective lens.

The slide housing 4, and in particular, the top housing member 6 thereof, is preferably formed from a plastic material, such as polystyrene, polycarbonate, an acrylic resin or cyclic olefin polymers and co-polymers, polyester, polyimide, and polysulfone. For digital imaging applications, and regardless of whether the top housing member 6 is clear, white, black, or some other color, the surface finish above the optical read area 26 should be optically smooth, because this surface's finish may affect image quality.

The slide housing 4 includes a lower base plate 16, which is preferably formed from a thin plastic material, such as polystyrene, polycarbonate, an acrylic resin, or cyclic olefin polymers and co-polymers, polyester, polyimide, and polysulfone, like the top housing member 6, and is preferably rectangular or square in shape and dimensioned to fit into and may protrude slightly from the bottom recess 32 formed in the top housing member 6. In a preferred form of the hematology test slide 2, there is a recessed lip 38 which surrounds the recess 32 formed in the bottom surface 34 of the top housing member 6. The four side edges of the base plate 16 are held in place against this recessed lip 38 formed in the bottom surface 34 of the top housing member 6 by an adhesive base gasket 14. The base gasket 14 also functions to seal the bottom recess 32 formed in the top housing member 6 and to effectively encapsulate, with the top housing member 6, the bottom and top cover slips 8, 12 and the blood or fluid sample contained within the viewing cell between them. More specifically, the base gasket 14 is square or rectangular in perimeter and is preferably formed from a double-sided adhesive tape, such as the transfer tape mentioned previously and preferably used for the spacer 10. The base gasket 14 also causes the edges of the bottom cover slip 12 to adhere to it.

Figure 2:
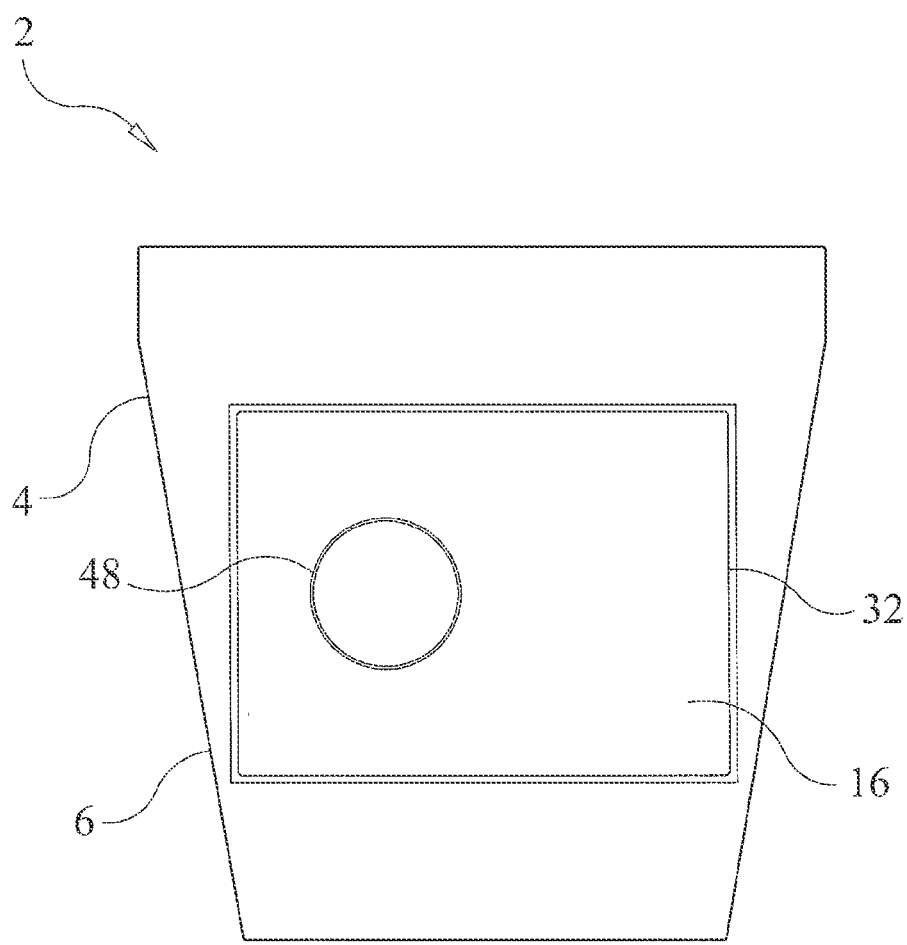
FIG. 2 is a bottom plan view of the hematology test slide of the present invention shown in FIG. 1.
Figure 3:
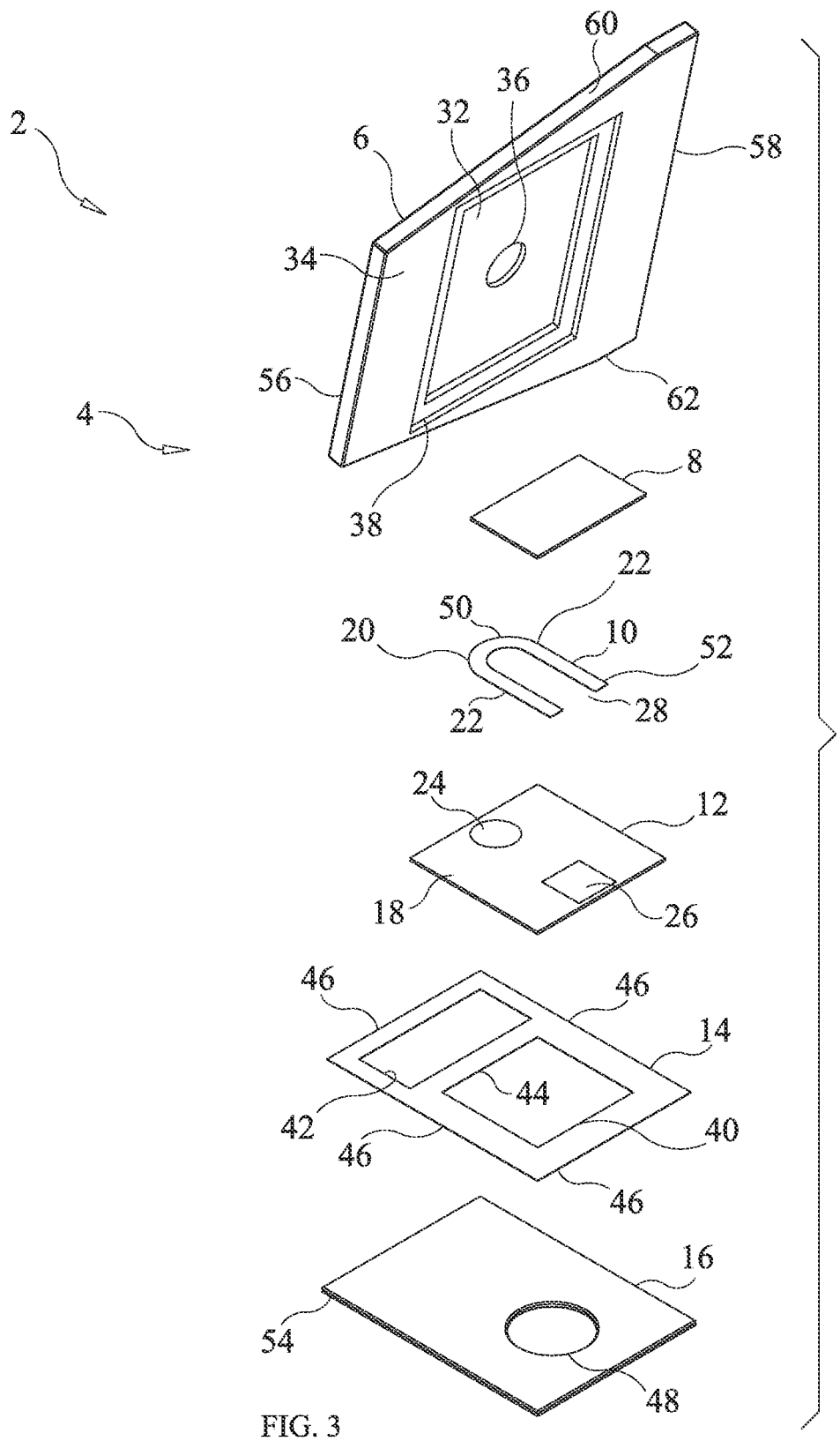
FIG. 3 is an exploded, isometric view (with the top housing rotated) of the hematology test slide of the present invention shown in FIGS. 1 and 2.
Figure 4:
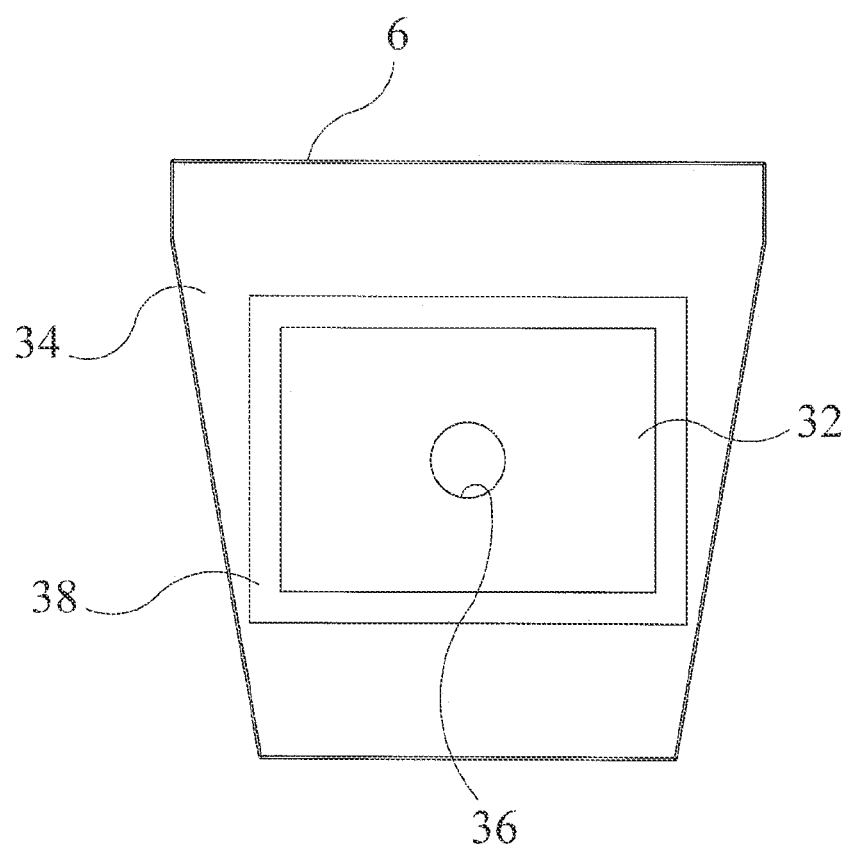
FIG. 4 is a bottom plan view of the top housing member of the hematology test slide of the present invention.
Figure 5:
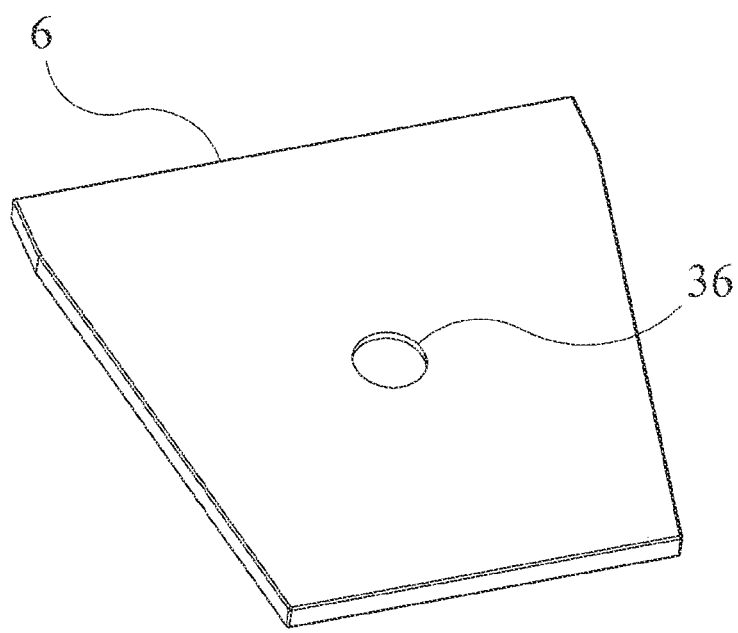
FIG. 5 is a top isometric view of the top housing member of the hematology test slide of the present invention shown in FIG. 4.
Figure 6:
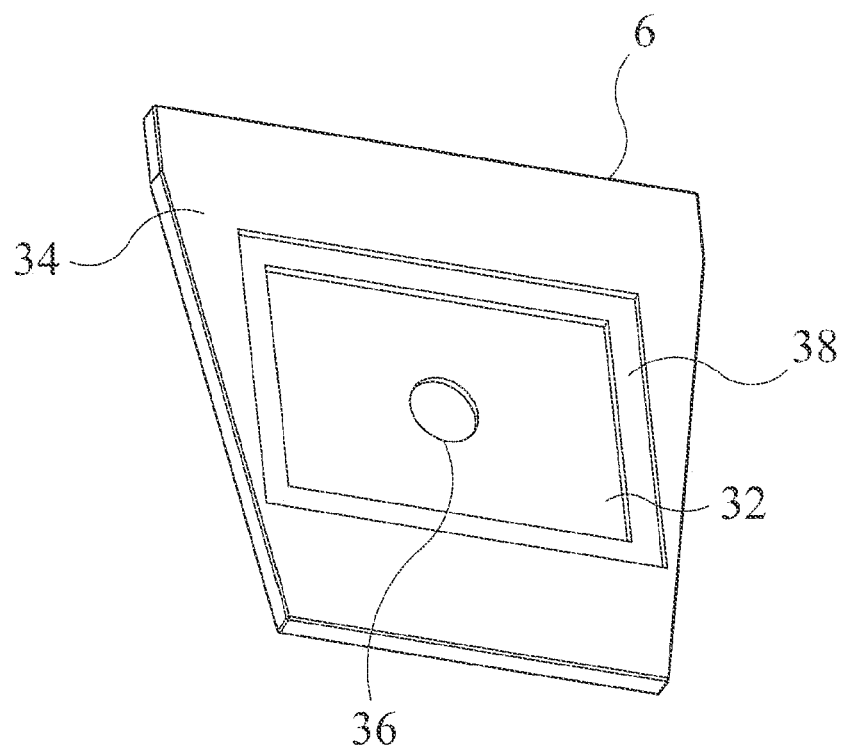
FIG. 6 is a bottom isometric view of the top housing member of the hematology test slide shown in FIGS. 4 and 5.
Figure 7:
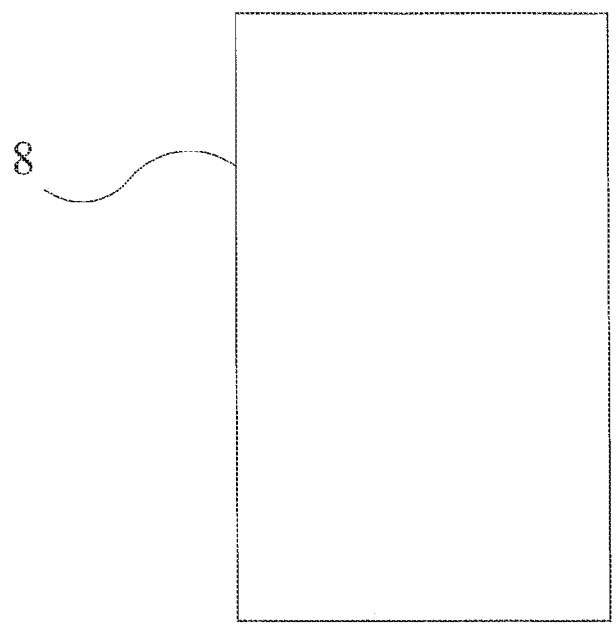
FIG. 7 is a bottom plan view of the top cover slip of the hematology test slide of the present invention.
Figure 8:
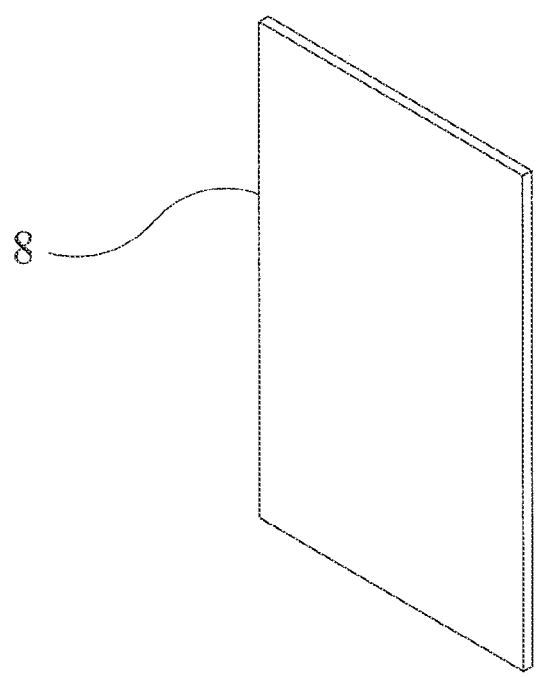
FIG. 8 is a bottom isometric view of the top cover slip of the hematology test slide of the present invention shown in FIG. 7.
Figure 9:
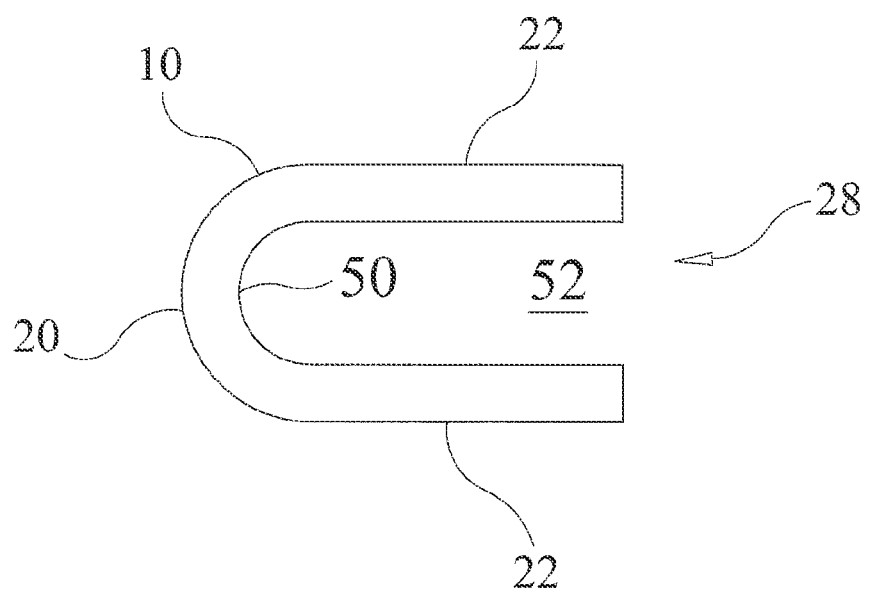
FIG. 9 is a bottom plan view of the spacer of the hematology test slide of the present invention.
Figure 10:
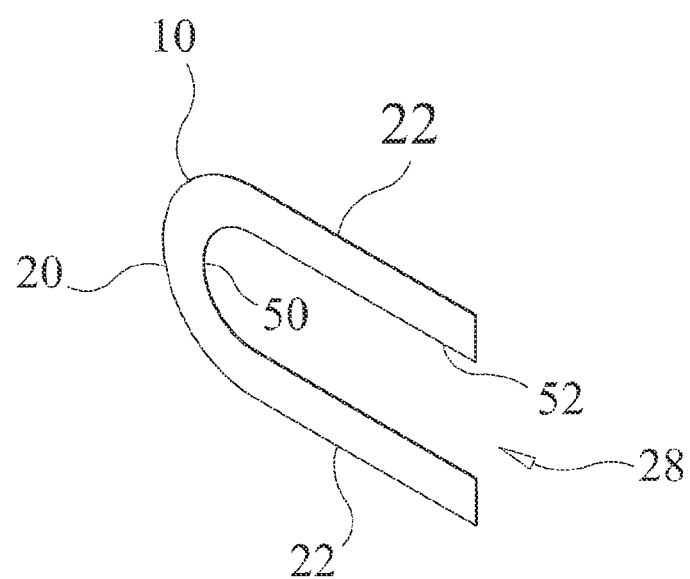
FIG. 10 is a bottom isometric view of the spacer of the hematology test slide of the present invention shown in FIG. 9.
Figure 11:
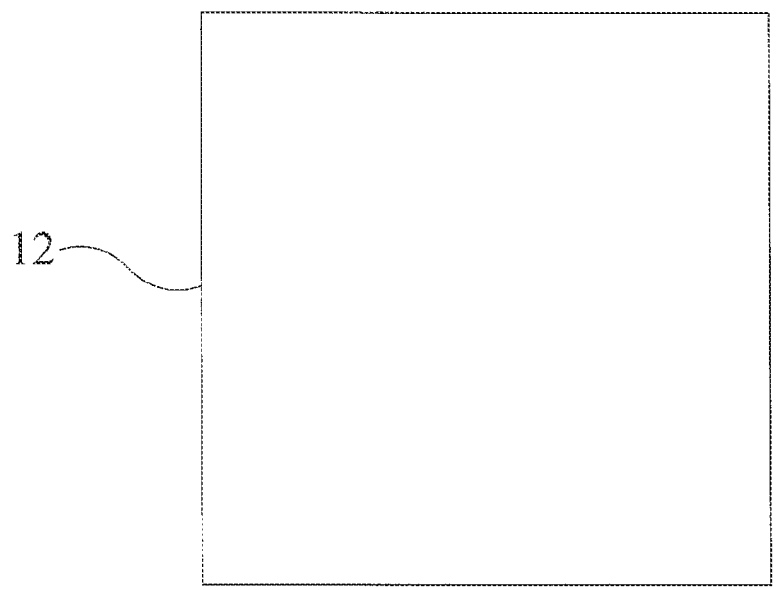
FIG. 11 is a bottom plan view of the bottom cover slip of the hematology test slide of the present invention.
Figure 12:
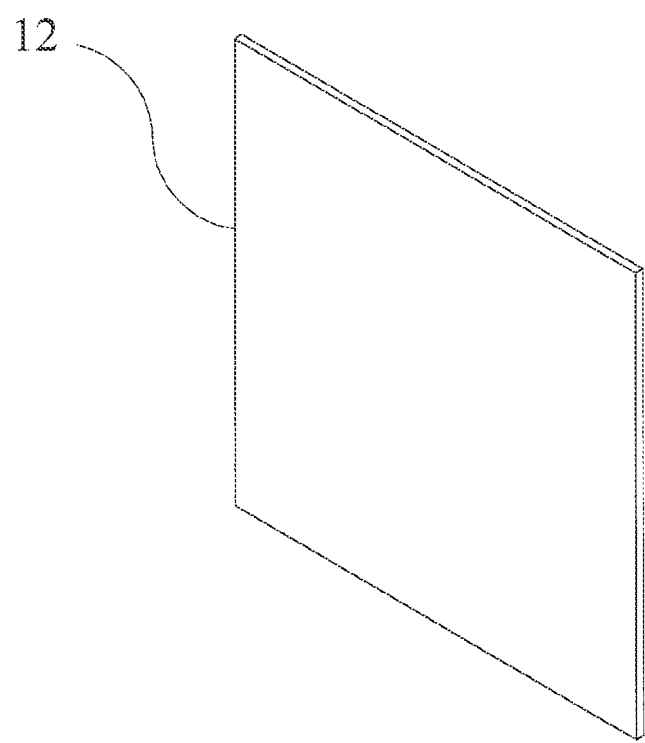
FIG. 12 is a bottom isometric view of the bottom cover slip of the hematology test slide of the present invention shown in FIG. 11.
Figure 13:
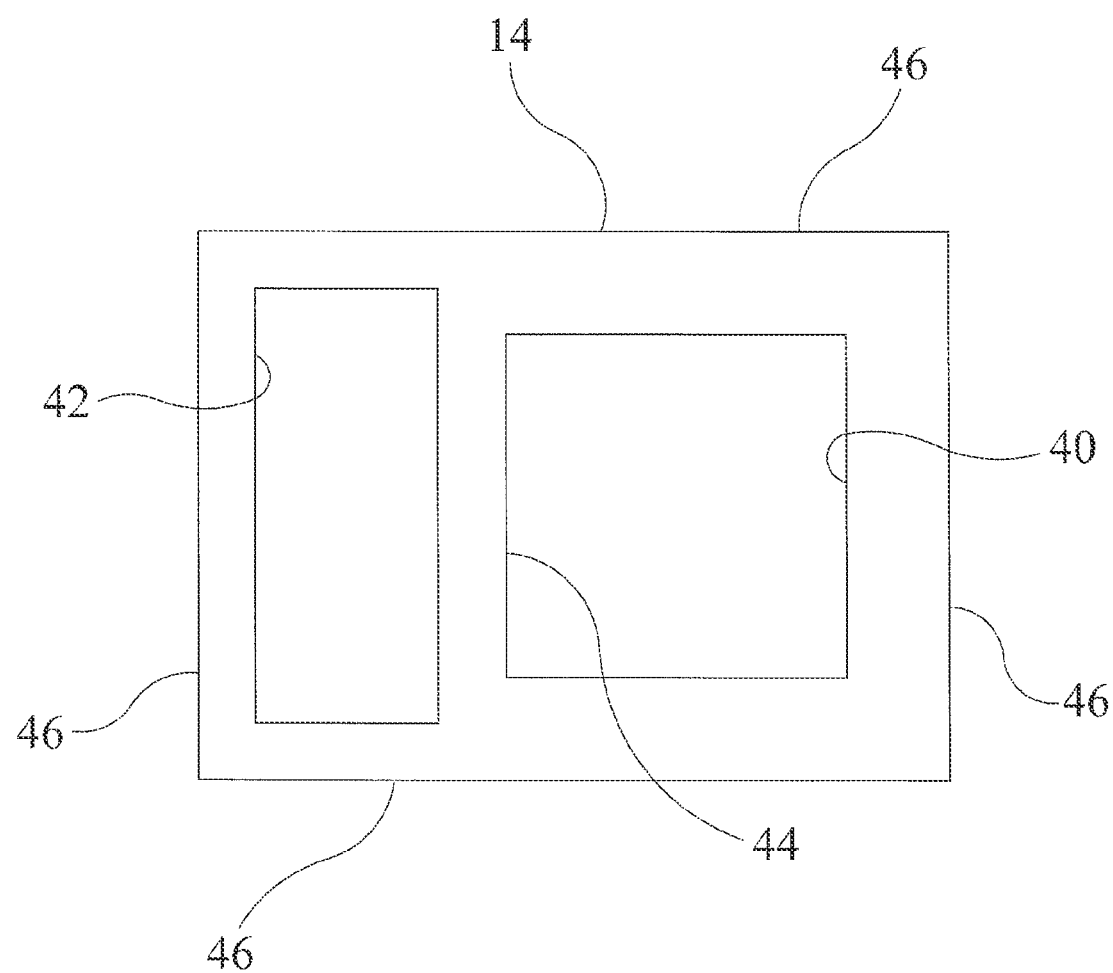
FIG. 13 is a bottom plan view of the base gasket of the hematology test slide of the present invention.
Figure 14:
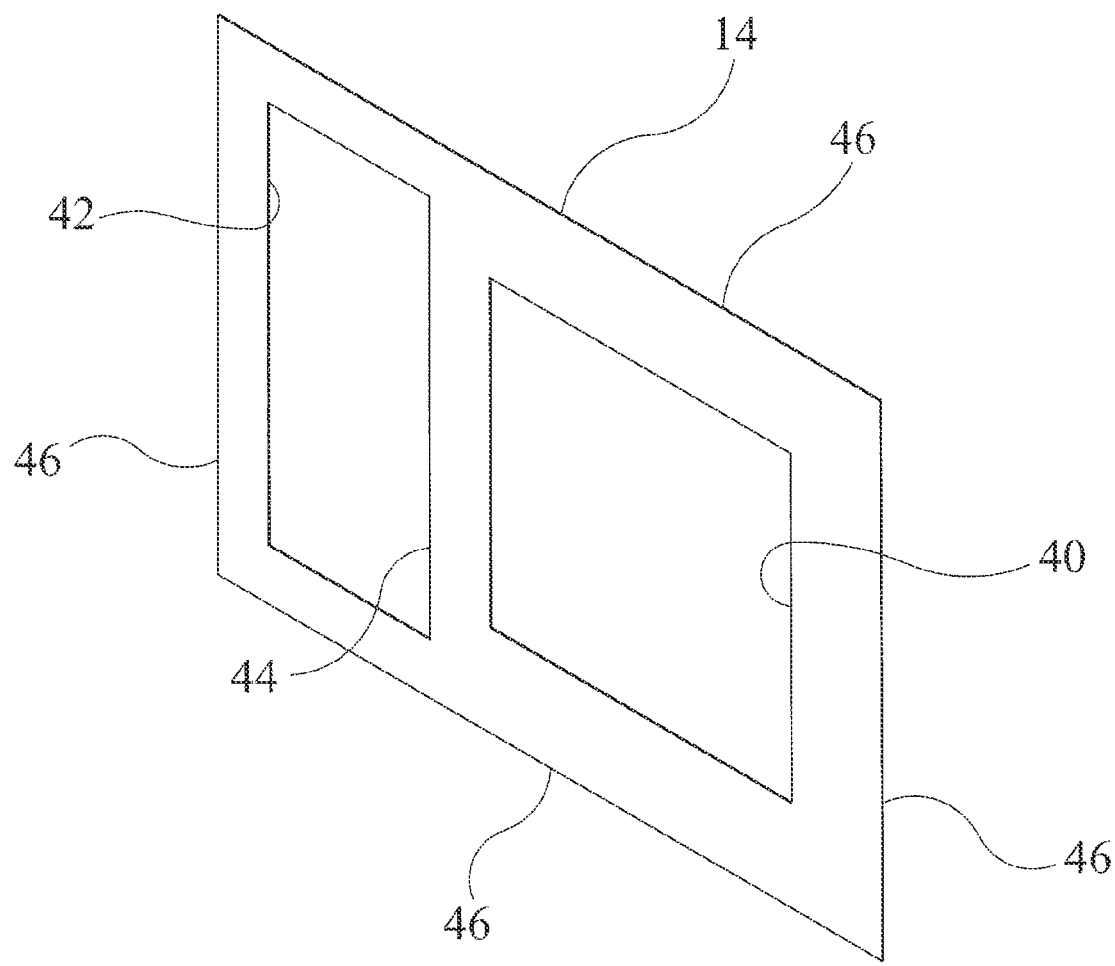
FIG. 14 is a bottom isometric view of the base gasket of the hematology test slide of the present invention shown in FIG. 13.
Figure 15:
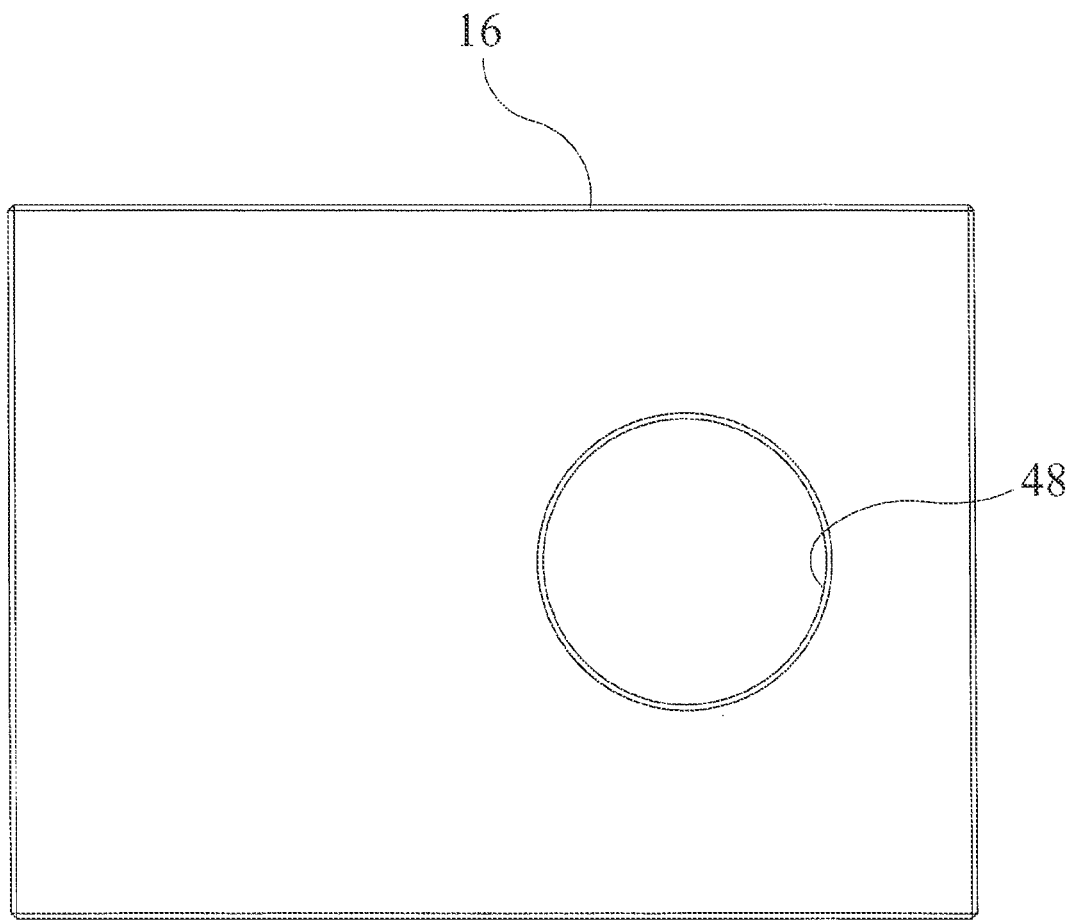
FIG. 15 is a bottom plan view of the base plate of the hematology test slide of the present invention.
Figure 16:
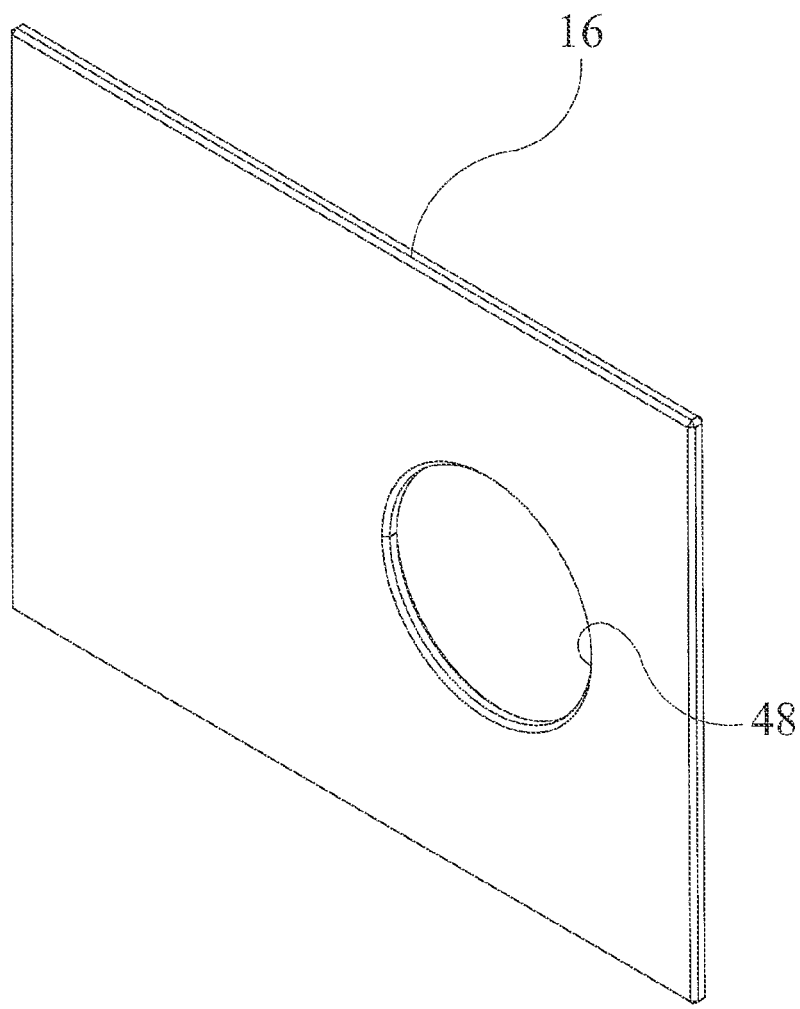
FIG. 16 is a bottom isometric view of the base plate of the hematology test slide of the present invention shown in FIG. 15.
Figure 17:
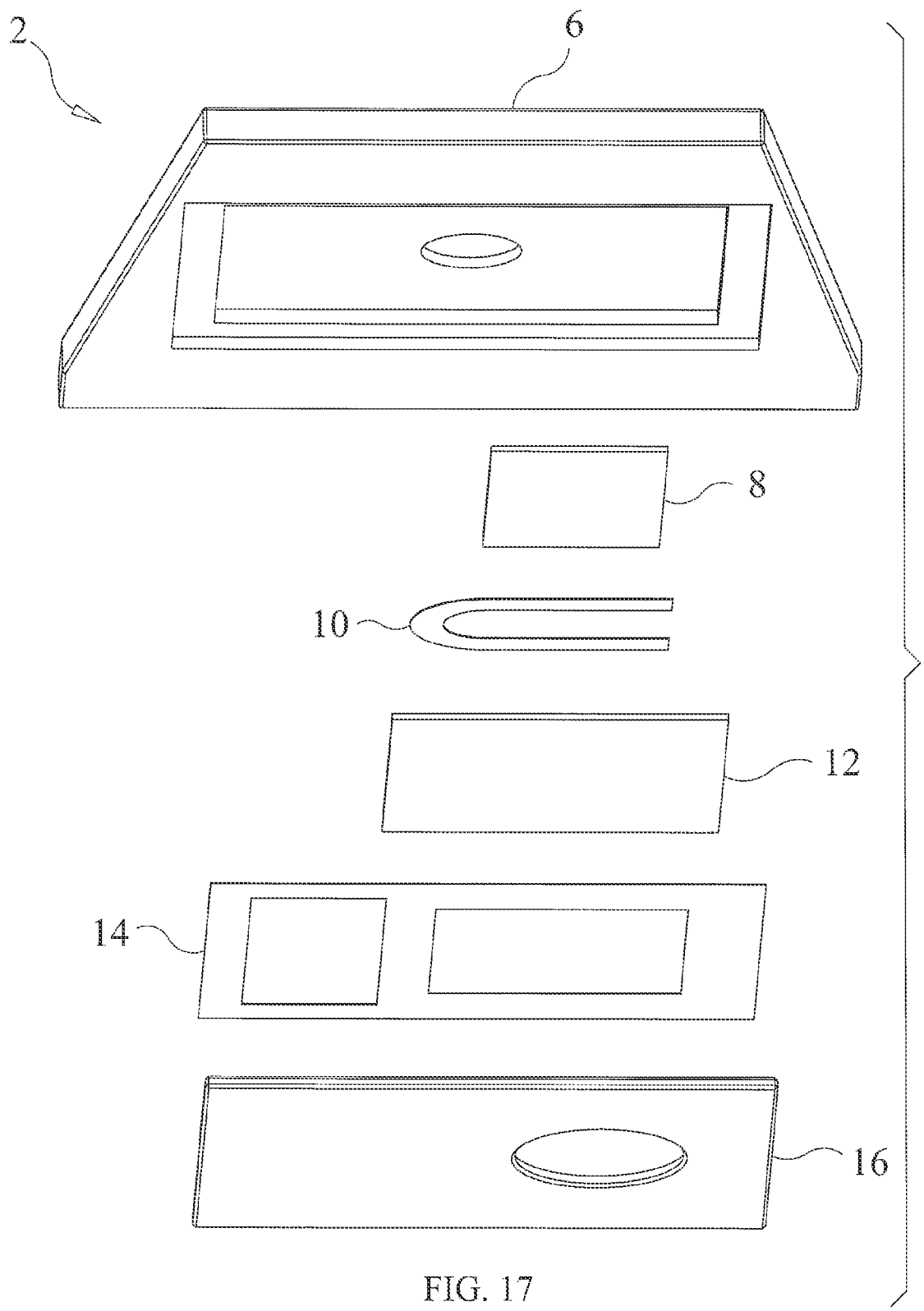
FIG. 17 is an exploded, bottom isometric view of the hematology test slide of the present invention, taken from a different perspective than that of FIG. 3.
Figure 18:
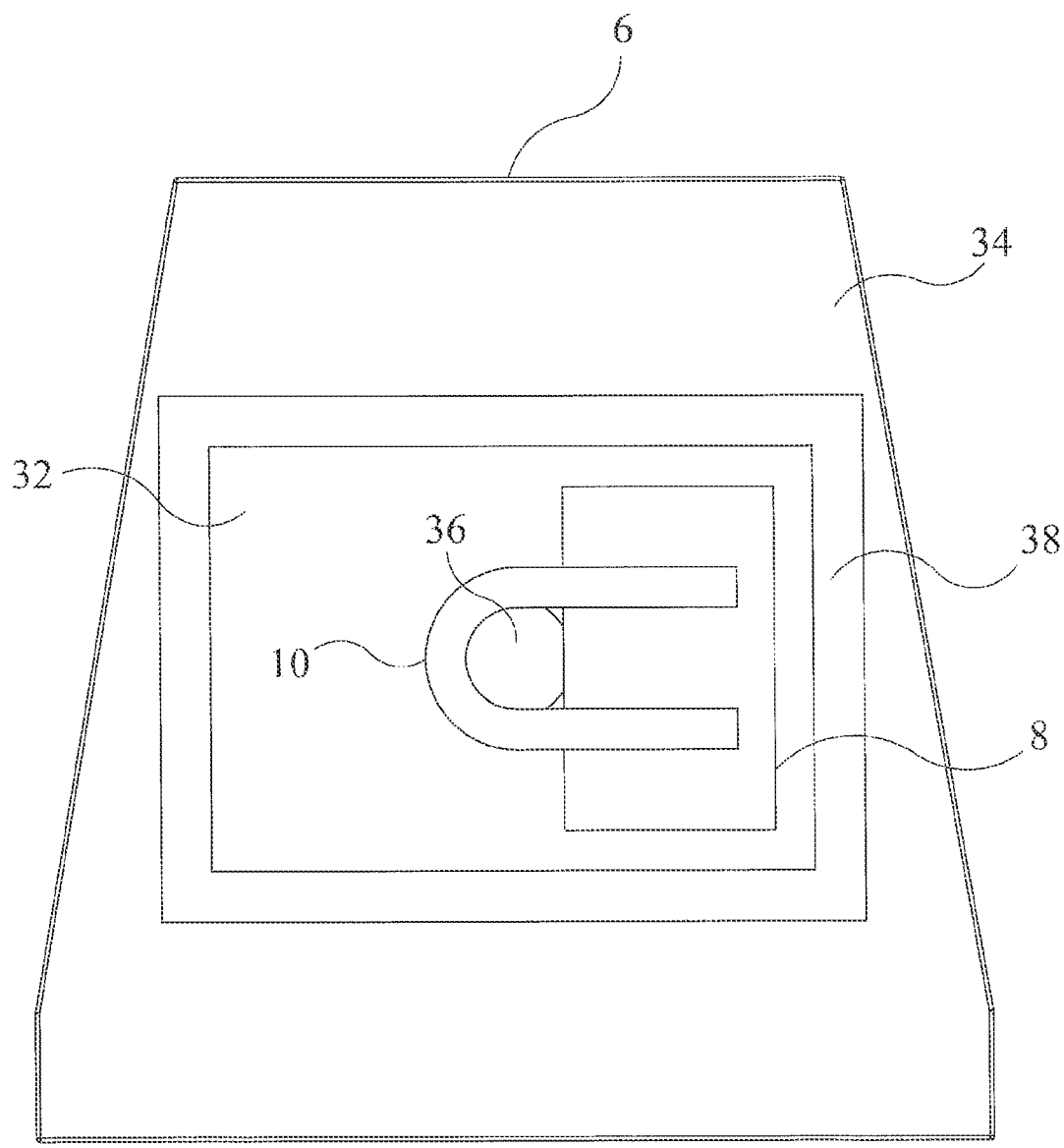
FIG. 18 is a bottom plan view of the hematology test slide of the present invention, showing the disposition of the top housing member, the top cover slip and the spacer, with the other components of the hematology test slide omitted for clarity.
Figure 19:
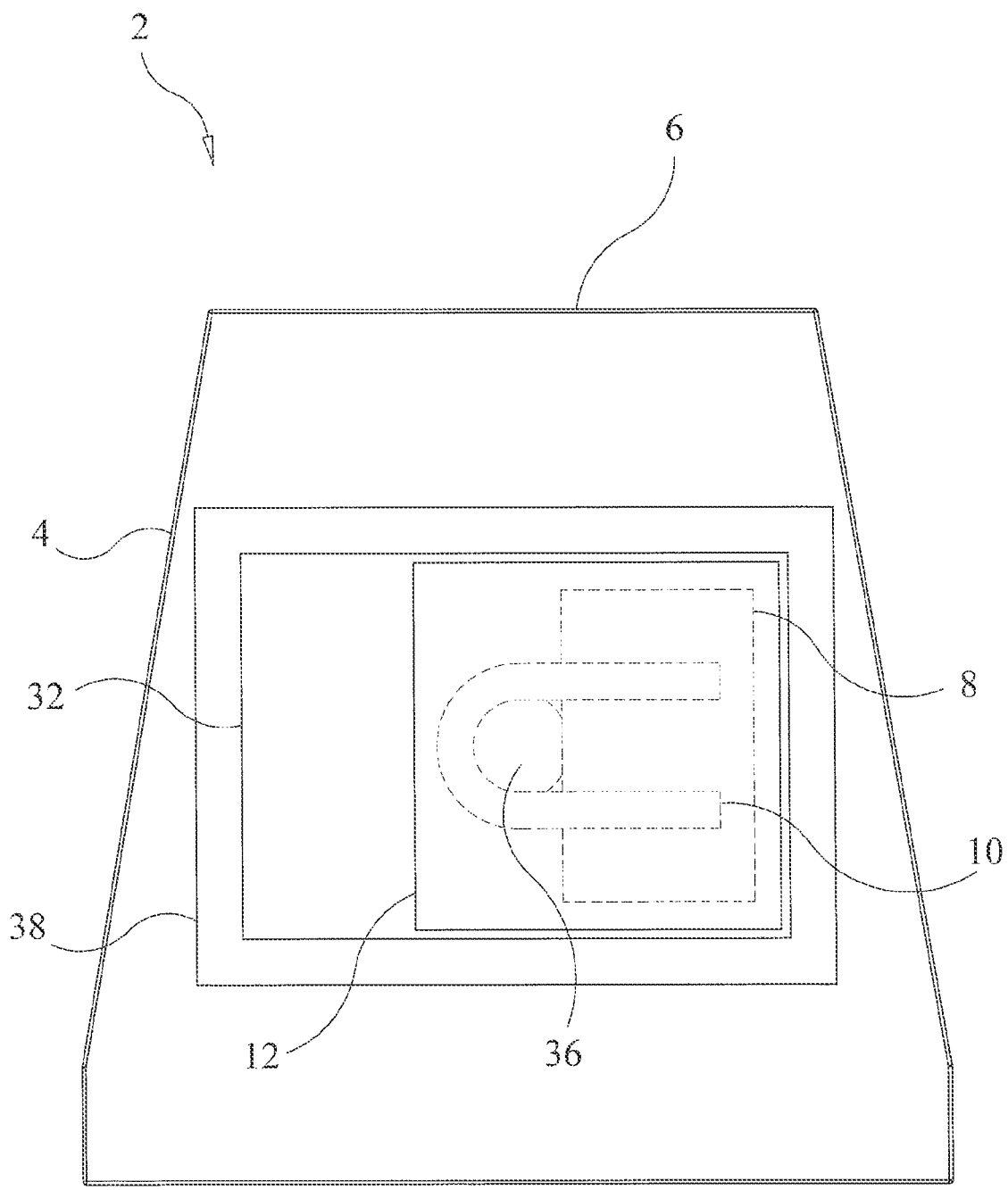
FIG. 19 is a bottom plan view of the hematology test slide of the present invention, showing the disposition of the top housing member, the top cover slip (in phantom), the spacer (in phantom) and the bottom cover slip, with the other components of the hematology test slide omitted for clarity.
Figure 20:
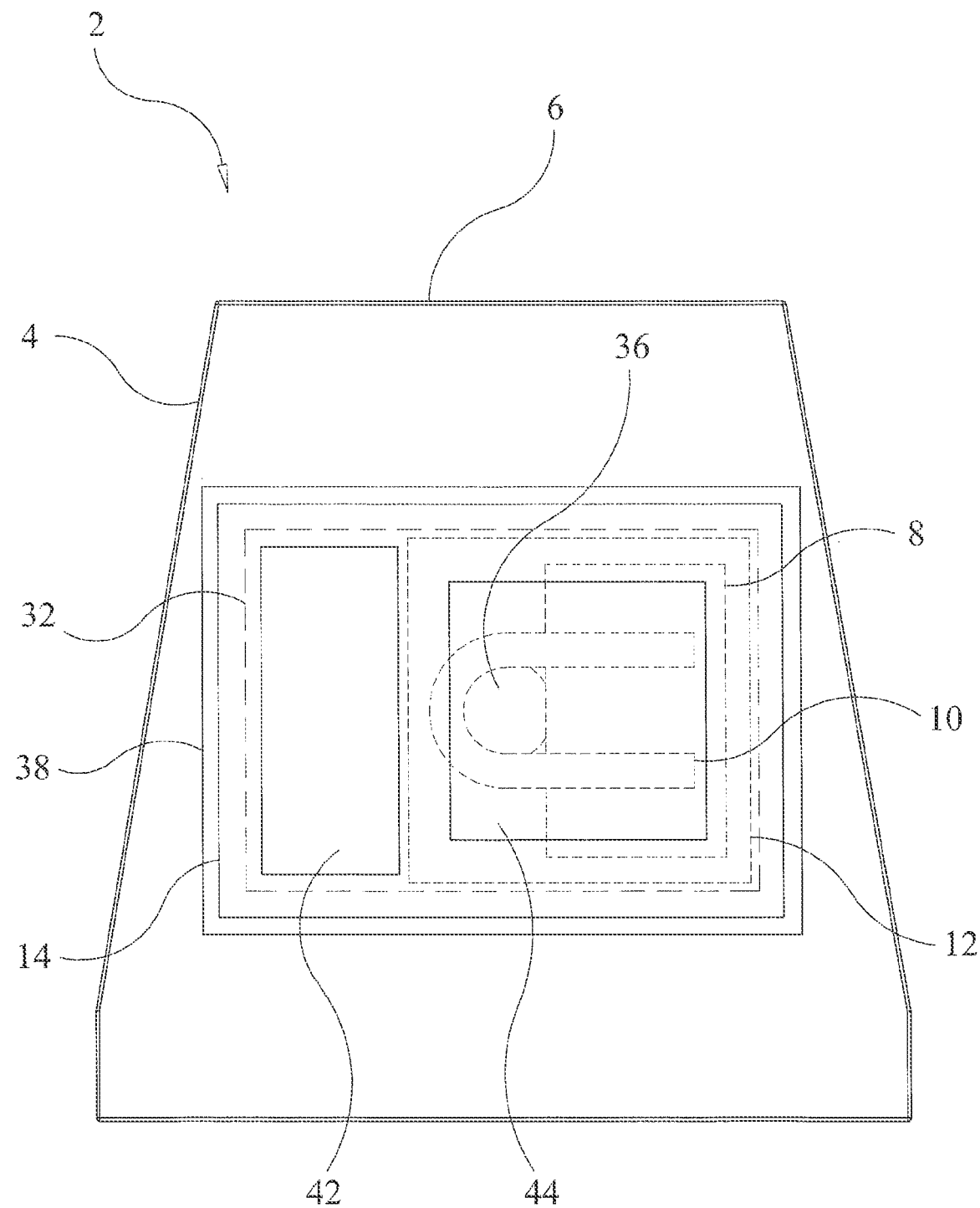
FIG. 20 is a bottom plan view of the hematology test slide of the present invention, showing the disposition of the top housing member, the top cover slip (in phantom), the spacer (in phantom), the bottom cover slip (in phantom) and the base gasket, with the other components of the hematology test slide omitted for clarity.
Figure 21:
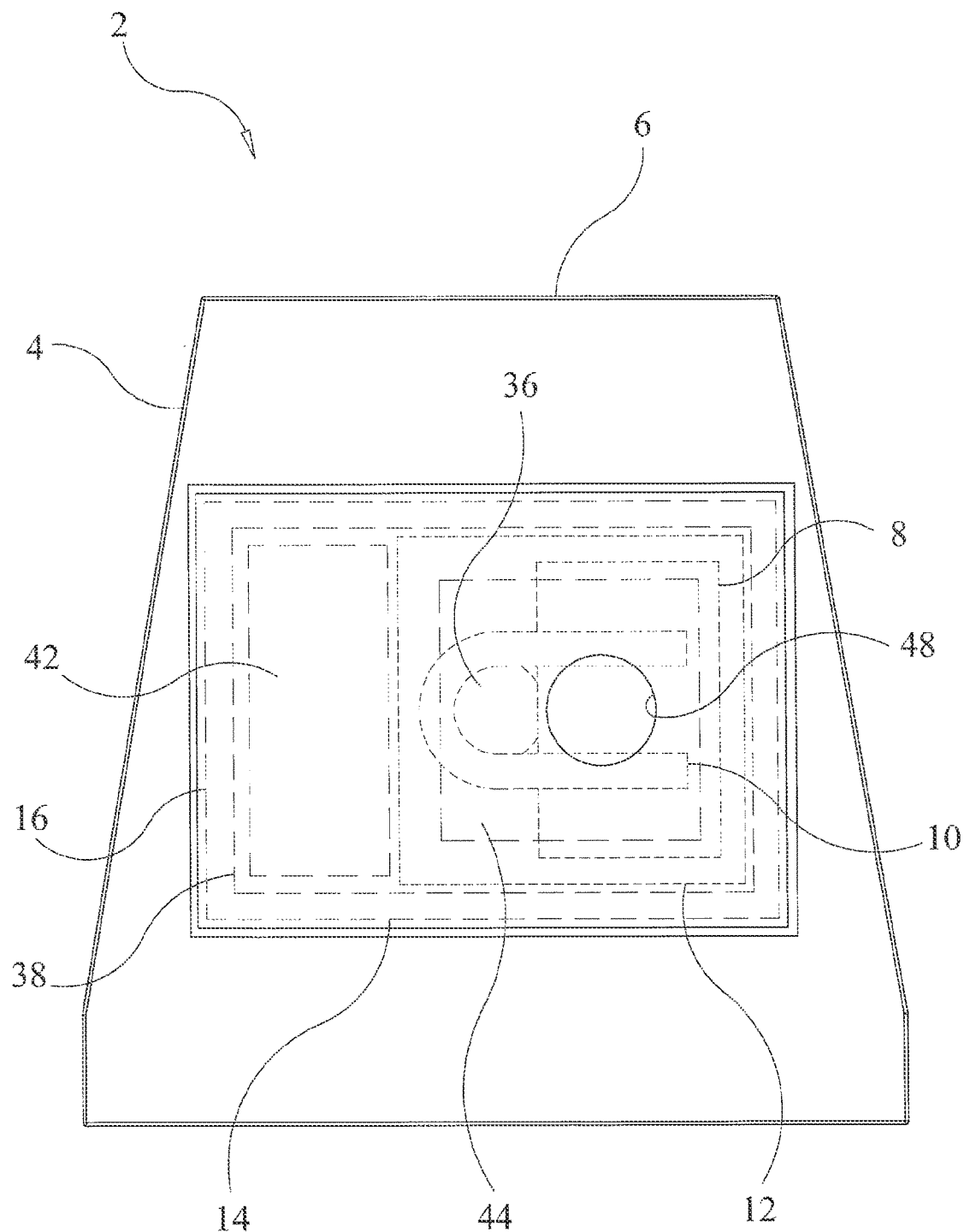
FIG. 21 is a bottom plan view of the hematology test slide of the present invention, showing the disposition of the top housing member, the top cover slip (in phantom), the spacer (in phantom), the bottom cover slip (in phantom), the base gasket (in phantom) and the base plate.

Even more specifically, the base gasket 14 is formed with at least one main open area 40 formed through its thickness (two adjacent open areas 40, 42, separated by a transverse section 44 of the gasket 14, are shown in FIG. 2). The main open area 40 of the gasket 14 is situated beneath the bottom cover slip 12 and the optical read area 26 defined between the parallel, straight legs 22 of the spacer 10. The main open area 40 is enclosed by three of the four peripheral side sections 46 of the base gasket 14 and the transverse section 44 of the gasket 14, with the bottom cover slip 12 adhering to the adhesive top surface of three of the four side sections 46 and the transverse section 44 of the gasket 14, and the top surface of the base plate 16 adhering to the adhesive bottom surface of the four peripheral side sections 46 and transverse section 44 of the base gasket 14. Exposed outer edge portions of the top surface of the peripheral side sections 46 of the base gasket 14 extending beyond the edges of the bottom cover slip 12 adhere to the recessed lip 38 formed in the bottom surface 34 of the top housing member 6 surrounding the recess 32 also formed therein to secure the base plate 16 to the bottom side of the top housing member 6 and the cover slips 8, 12 and spacer 10 within the recess 32 formed in the top housing member 6 in a protective and fully encapsulated fashion.

Open area 40 of base gasket 14 is necessary to keep the transfer tape out of the optical pathway between optical read area 26 with the optical module located underneath. Open area 42 may, in some embodiments, not exist at all. One advantage of including open area 42 is that it may reduce the likelihood of the base of recess 32 of top housing member 6 sticking to base gasket 14, which would potentially distort the slide.

The base plate 16 has formed through its thickness an optical read opening 48. The optical read opening 48 is situated in alignment with the optical read area 26 defined between the parallel, straight legs 22 of the spacer 10. The optical read opening 48 is preferably about five (5) millimeters in diameter, or less, and is preferably laterally offset from the sample deposit opening 36 formed in the top housing member 6 of the slide housing 4. In this way, very little glass of the bottom cover slip 12 will be exposed through the optical read opening 48, in order to protect the slide 2 from damage and contamination and the user from injury. Furthermore, it is preferred to have such an optical read opening 48 formed in the base plate 16 so that optical measurements may be made directly on the read area 26 through the bottom cover slip 12, without the inaccuracies associated with making measurements through a plastic material that are compromised by light scattering, reflection and the like. Of course, it is envisioned to be within the scope of the present invention to form the base plate 16 from a light transmissive material, such as the plastics mentioned above, and to compensate for any inaccuracies in optical measurements caused thereby.

The base plate 16, with the top housing member 6 of the slide housing 4, completely seals the pipetted fluid sample within the slide 2, except for the sample deposit opening 36. In addition to providing a liquid and vapor seal for the inside components of the slide 2, the base plate 16, to which the bottom cover slip 12 is adhered by the base gasket 14, insures that the bottom cover slip 12 is substantially parallel to the bottom surface of the slide housing 4 and not angled or sloped thereto, so that a more accurate hematology measurement may be made by the reflectometer, fluorometer, digital imaging camera or other optics module of an automated chemistry analyzer situated below the hematology test slide 2. This is an important feature because, if the optical axis of the optics module of the chemistry analyzer is aligned perpendicularly to the bottom cover slip 12, then the cells to be counted will be located on top of the bottom cover slip 12 and the entire field of view of the cells can be brought into optimal focus with, preferably, only one axis of focus adjustment.

For precision imaging, one axis focus adjustment is obtained by ensuring that the optical axis of the imaging optics is perpendicular to a precision sapphire window of the optics module that the base plate 16 of the slide housing 4 rests upon. If base plate 16 has highly parallel top and bottom faces, then the base gasket 14 contributes negligibly to the optical wedge or non-parallelism of the optical system, and if the base plate 16 is pressed flat against the window, then the bottom cover slip 12 is also normal to the optical axis. In this case, the only expected adjustment needed between one slide housing 4 and the next will be to accommodate minor variations in base plate 16, base gasket 14, and bottom cover slip 12 thicknesses. With a well-aligned optical system, this adjustment can be achieved by one axis adjustment of the spacing between the optical system and the sapphire window which, in turn, helps keep the cost of an imaging optical module relatively low.

The structure of the hematology test slide 2 of the present invention, and a method of conducting a hematology measurement using the hematology test slide 2 on an automated clinical instrument, will now be further described.

A hematology test slide 2 constructed in one form of the present invention includes a first cover slip, which may be the top cover slip 8, a second cover slip, which may be the bottom cover slip 12, and a spacer 10 interposed between the first cover slip 8 and the second cover slip 12. The spacer 10 has a closed end portion 50 and an open end portion 52 situated opposite the closed end portion 50, and is preferably U-shaped, meaning that it has a curved or straight transverse section at the closed end portion 50. The open end portion 52 is defined by a pair of spaced apart legs 22 extending outwardly from the closed end portion 50. The closed end portion 50 interiorly defines a sample deposit area 24, and the pair of spaced apart legs 22 of the open end portion 52 defines between the legs 22 an optical read area 26. The optical read area 26 of the spacer 10 is bounded above and below, respectively, by the first and second cover slips 8, 12, and the sample deposit area 24 is uncovered by the first cover slip 8 to allow a fluid sample to be deposited onto the sample deposit area 24.

Preferably, the closed end portion 50 of the spacer 10 includes a curved, semi-circular section 20 or a straight transverse section (not shown), and the legs 22 of the open end portion 52 of the spacer 10 are straight members parallelly disposed to one another and which extend from the curved, semi-circular section 20 or straight transverse section of the closed end portion 50 of the spacer 10.

The spacer 10 has a top surface and an opposite bottom surface, and each of the first cover slip 8 and the second cover slip 12 has a top surface and an opposite bottom surface. At least a portion of the top surface of the spacer 10 is in contact with the bottom surface of the first cover slip 8, and the bottom surface of the spacer 10 is in contact with the top surface of the second cover slip 12.

At least a portion of the top surface of the spacer 10 which is in contact with the bottom surface of the first cover slip 8 is adhesively joined to the bottom surface of the first cover slip 8. The bottom surface of the spacer 10 is adhesively joined to the top surface of the second cover slip 12. Preferably, the spacer 10 is formed from a double-sided adhesive tape, such as a transfer tape.

The bottom surface of the first cover slip 8 and the top surface of the second cover slip 12 are spaced apart from each other at the optical read area 26 a predetermined distance. The spacer 10 has a specific thickness which defines the predetermined distance which the bottom surface of the first cover slip 8 is spaced from the top surface of the second cover slip 12 over at least a portion of the spacer 10 proximal to the optical read area 26.

In one preferred form of the hematology test slide 2, the thickness of the spacer 10 over the at least portion thereof proximal to the optical read area 26 is between about three (3) microns and about five (5) microns. In another preferred embodiment of the test slide 2, the thickness of the spacer 10 at at least the read area 26 is between about five (5) microns and about fifty (50) microns. In yet another preferred form of the test slide 2, the thickness of the spacer 10 over the at least portion thereof proximal to the optical read area 26 is between about fifty (50) microns and about two hundred and fifty (250) microns. Alternatively, the thickness of the spacer 10 over the at least portion thereof situated at the optical read area 26 is between about twenty-five (25) microns and about fifty (50) microns.

The first cover slip 8 and the second cover slip 12 are spaced apart from each other at the optical read area 26 a predetermined distance to define a fluid holding cell having a measurable volume between the first and second cover slips 8, 12 situated at the optical read area 26.

The hematology test slide 2 of the present invention may further include a slide housing 4. The slide housing 4 has a top housing member 6 and a bottom housing member 54 joined to the top housing member 6. The top and bottom housing members 6, 54 define a cavity in which is received the first cover slip 8, the spacer 10 and the second cover slip 12.

Preferably, the slide housing 4 is generally trapezoidal in overall shape, and includes a front portion 56, a rear portion 58 situated opposite the front portion 56, a first side portion 60 and a second side portion 62 situated opposite the first side portion 60, where the front and rear portions 56, 58 are generally parallel to each other and the rear portion 58 is longer than the front portion 56, and the first and second side portions 60, 62 extend between the front and rear portions 56, 58 in a mutually non-parallel direction. In this way, the hematology test slide 2 of the present invention has the same overall trapezoidal shape as that of the chemical reagent test slides and immunoassay test slide disclosed in the aforementioned U.S. patents and published U.S. patent applications. The housing 4 may include an offset indexing notch (not shown) on the front portion 56 thereof for proper orientation of the test slide 2 on an analytical instrument, and lateral side recesses (not shown) formed in the first and second side portions 60, 62 used for loading the test slides on an analytical instrument, in the same manner and in the same locations as the notch and lateral side recesses included in the dry chemistry test slides and immunoassay test slide disclosed in the aforementioned U.S. patents and published U.S. patent applications.

The top housing member 6 of the slide housing 4 has a planar structure and includes a top side and an opposite bottom side 34. The bottom side 34 of the top housing member 6 has formed therein a recess 32 which at least partially defines the cavity of the slide housing 4 for receiving the first cover slip 8, the spacer 10 and the second cover slip 12.

The top housing member 6 includes a sample deposit opening 36 formed through the thickness thereof. The sample deposit opening 36 is situated in alignment and in fluid communication with the sample deposit area 24 of the spacer 10 and for receiving through the sample deposit opening 36 a fluid sample.

The bottom housing member 54 includes a base plate 16 which is planar in form. The base plate 16 is affixed to the top housing member 6 to encapsulate within the cavity of the slide housing 4 the first cover slip 8, the spacer 10, the second cover slip 12 and any fluid sample residing in the optical read area 26 of the spacer 10.

The base plate 16 includes an optical read opening 48 formed through the thickness thereof. The optical read opening 48 in the base plate 16 is situated in alignment with the optical read area 26 of the spacer 10. Preferably, the optical read opening 48 formed in the base plate 16 is offset from the sample deposit opening 36 formed in the top housing member 6 so as to be in non-alignment with the sample deposit opening 36.

The hematology test slide 2 of the present invention also preferably includes a base gasket 14. The base gasket 14 is interposed between the second cover slip 12 and the base plate 16. The base gasket 14 is preferably adhesively joined to the second cover slip 12 and the base plate 16. Even more preferably, the base gasket 14 is formed from a double-sided adhesive tape, such as a transfer tape, to adhere the base plate 16 to the second cover slip 12. The base gasket 14 further adheres the base plate 16 to the top housing member 6.

The top housing member 6 of the slide housing 4 may be substantially opaque over at least a portion thereof situated in alignment with the optical read area 26 of the spacer 10 to serve as a backdrop for optical measurements conducted on a fluid sample residing within the optical read area 26. Alternatively, the first cover slip 8 may be substantially opaque over at least a portion thereof situated in alignment with the optical read area 26 of the spacer 10 to serve as such a backdrop for optical measurements conducted on a fluid sample residing within the optical read area 26.

Preferably, each of the first cover slip 8 and the second cover slip 12 is formed from a hydrophilic material. Additionally, both cover slips 8, 12, or at least the second cover slip 12, is formed from a light transmissive material. Preferably, each of the first cover slip 8 and the second cover slip 12 is formed from glass. At least the second cover slip 12 has a preferred thickness of between about 170 microns and about 180 microns, although each cover slip 8, 12 preferably has this thickness.

In accordance with the present invention, a method of conducting a hematology measurement on an automated clinical instrument which is adapted to use dry chemistry test slides will now be described. The method includes the step of placing a hematology test slide 2 on the automated clinical instrument, the hematology test slide 2 having the structure described previously, with or without the protective housing 4. A fluid sample is deposited onto the sample deposit area 24 of the spacer 10 of the hematology test slide 2 and is allowed to flow by capillary action between the first cover slip 8 and the second cover slip 12 from the sample deposit area 24 of the spacer 10 of the hematology test slide 2 to the optical read area 26 of the spacer 10 of the hematology test slide 2. Then, an optical measurement is conducted on the fluid sample residing in the optical read area 26 of the hematology test slide 2 using a reflectometer, fluorometer or a digital imaging camera, for example.

It is envisioned that the hematology test slide 2 of the present invention will be used with similarly-dimensioned chemical reagent test slides and immunoassay test slides, such as described previously in the aforementioned patents and U.S. applications, on the same analyzer, which analyzer transports the various slides in a circular path below a sample metering device and above an optics module, which could be a reflectometer, fluorometer or a digital imaging camera. Accordingly, it is preferred to arcuately offset the optical read opening 48 formed in the base plate 16 from the sample deposit opening 36 formed in the top housing member 6. Preferably, the optical read opening 48 is offset tangentially from the sample deposit opening 36 along the same are defined by the radius of the circular path along which the test slides 2 move by between about 2 mm and about 6 mm between the centers of the openings 36, 48. By offsetting the optical read opening 48 from the sample deposit opening 36 on the hematology slide 2, not only is it possible to define an accurate volume within the optical read area 26, but also a solid portion of the top housing member 6 can, if opaque, act as a backdrop to the optical read area 26 situated directly below it.

The slide 2 of the present invention described herein is capable of conducting several hematology tests: a red blood cell (RBC) count and mean corpuscular volume (MCV) measurement; a platelet (PLT) count; a hemoglobin (HGB) concentration measurement; and a white blood cell (WBC) count with a three-part differential (granulocytes, lymphocytes and monocytes) or even a five-part differential (lymphocytes, monocytes, neutrophils, basophils and eosinophils). Other relevant hematology quantities can be derived from these basic measurements, including hematocrit (HCT) and the red blood cells' mean corpuscular hemoglobin concentration (MCHC). More advanced hematology information, for example, the five-part differential white blood cell (WBC) counts and reticulocyte counts, may also be obtained from such measurements using the hematology test slide 2 of the present invention.

A specific slide 2 may be structured to carry out a particular measurement mentioned above, or a single hematology slide 2 may be used to perform all of these functions. The slides 2 could be essentially identical except possibly for the volume of the viewing cell defined by the field of view of a digital imaging camera and the spacing between the top and bottom cover slips 8, 12. As mentioned previously, a reflectometer or fluorometer may be used to make such measurements, or a hematology optics module comprising an inverted, dark field microscope may be used for digital imaging of the slide 2.

Although a single hematology slide 2 may be used to conduct an RBC count, a PLT count and a WBC count, the sample dispensed onto the slides may be different for each kind of measurement.

For red blood cell (RBC) counting, a portion of the sample may be diluted and may be stained (for better contrast and for identification of reticulocytes), but not lysed. The red blood cells may also be sphered to make them easier to count by adding a sphering agent to the blood sample, such as a zwitterionic detergent. The hematology slide 2, for counting red blood cells, may have a very narrow detection cell defined by and between the top and bottom cover slips 8, 12, on the order of about five (5) microns to about ten (10) microns. In this case, the very narrow vertical aspect of the cell thickness makes it unlikely that one red blood cell will obstruct the view, and counting, of a red blood cell above it.

However, the disadvantage of such a vertically narrow cell is that relative spacing errors between the top and bottom cover slips become more significant. For this reason, the detection cell spacing is preferably between about ten (10) microns and about fifty (50) microns. By adequate dilution of the blood sample, approximately one (1) part blood with ninety-nine (99) parts diluent, it is also possible to almost completely prevent red blood cells from stacking upon one another.

For white blood cell (WBC) and platelet (PLT) counting, a portion of the sample is treated with a red blood cell lysis reagent, diluted, and possibly stained or otherwise labeled. Lysis causes the red blood cells to burst, spilling their contents and preferably breaking their cell walls into tiny fragments invisible to the microscope. The stain may be a colorimetric colloid or dye, or an intercalating fluorescent or colorimetric dye, but labeled antibody conjugates are also contemplated. The stain or label may simply provide a wavelength-specific absorbance (e.g., a colloidal gold antibody conjugate) or it may also fluoresce, allowing detection by illumination and detection at specific wavelengths. The purpose of the stain or label is to enhance differentiation of white blood cell types, for example, between granulocytes, lymphocytes and monocytes. A combination of morphology detection and stains or labels may be employed for white blood cell differentiation.

Since the total concentration of white blood cells is about 1,000 times less than red blood cells in a healthy animal, the vertical aspect of the slide's detection cell is approximately two- to ten-fold greater than in a hematology test slide 2 specifically designed for red blood cell tests. As mentioned previously, for white blood cells, the slide 2 may have a cell thickness or depth of between about fifty (50) microns and about two hundred fifty (250) microns. The greater volume of the viewing cell increases the counting accuracy for the relatively rare white blood cells without much likelihood that one white blood cell will be hidden behind another white blood cell. Also, the white blood cells in the sample will rapidly fall to the bottom of the thicker or deeper detection cell, making them easier to count even if the microscope's depth of field is low. An inverted microscope with oblique illumination is preferably used to count red blood cells and white blood cells in the blood sample. For the detection of hemoglobin content of a lysed, most likely diluted whole blood sample, a reflectometer or fluorometer, rather than an inverted microscope, is preferably used.

In order to further increase the WBC count, it is possible to image adjacent portions of the optical read area 26, increasing the total count by approximately a multiple of the non-overlapping images obtained. The adjacent portions need not be contiguous. Likewise, overlapping images may be obtained too, as long as specific cells appearing in more than one image are only counted once. One preferred configuration for WBC counting employs a spacing between the top and bottom cover slips 8, 12, of seventy-eight (78) microns and three adjacent side-to-side images for counting. In this case, and with a field of view of approximately 1.28 mm×0.96 mm (expected with a 5× objective and a ½" digital imaging sensor), and a whole blood sample diluted one (1) part blood to one and seven eighths (1.875) parts lysing agent, even a relatively low normal WBC count sample of 5000 total WBC per microliter would be expected to provide about five hundred (500) counted WBCs.

Figure 22:
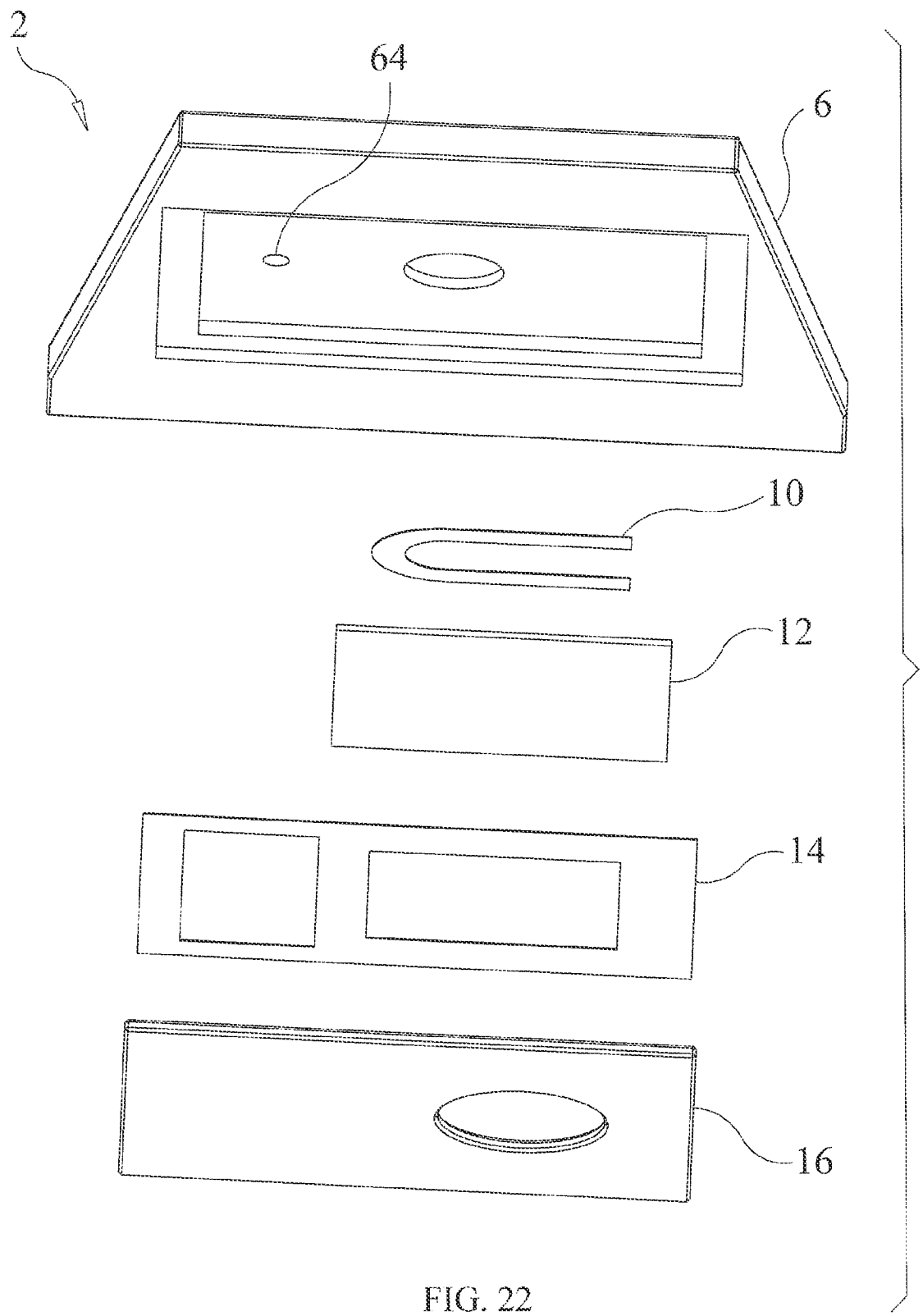
FIG. 22 is an exploded, bottom isometric view of a hematology test slide constructed in accordance with another form of the present invention.

In another version of the hematology test slide 2 of the present invention, which is shown in FIG. 22 of the drawings, the top cover slip 8 has been omitted, as the top housing member 6 functions in this embodiment as the top cover slip 8 to define with the bottom cover slip 12 and the spacer 10 situated therebetween a cell having a measureable volume for receiving an aliquot of a blood sample. As in the previously described embodiment of the hematology test slide 2 shown in FIGS. 1-21, the spacer 10 interposed between the bottom surface 34 of the top housing member 6 and the top surface of the bottom cover slip 12 defines the thickness or depth of the cell for holding the blood sample, and further adheres together the top housing member 6 and the bottom cover slip 12 and further defines the region, that is, the sample deposit area 24, into which the sample is pipetted. The top housing member 6 could be formed from the same or similar hydrophilic materials as the top cover slip 8 omitted from this embodiment described previously. Also, in the five-component embodiment or the six-component embodiment described previously, or with the four-component version of the hematology test slide 2 described below, the top housing member 6 may include an air vent hole 64 formed through its thickness and situated outside the area where the spacer 10 contacts the top housing member 6 and preferably adjacent to the closed end portion 50 of the spacer 10 and opposite the open end portion 52 of the spacer 10 (see FIG. 22). The air vent hole 64 is provided to help the slide 2 fill with sample and to promote the capillary flow of the sample from the sample deposit area 24 to the optical read area 26.

Furthermore, although shown in FIG. 22 of the drawings, this embodiment of the hematology test slide 2 may further omit the base gasket 14 so that the hematology test slide 2 is primarily constructed of four components: the top housing member 6 of the slide housing 4; the spacer 10, which is preferably U-shaped; the bottom cover slip 12; and the base plate 16. For a hematology test slide having a maximum specified thickness, such an embodiment would provide a greater depth and volume for holding a liquid sample.

More specifically, it is preferred that the hematology test slide 2 of the present invention has the same or similar overall dimensions, including thickness, as those of chemical reagent test slides and immunoassay test slides described previously so that they may be used and are compatible with the same dry chemistry analytical instrument that runs clinical chemistry, electrolyte and immunoassay tests on a single whole blood sample. For example, if the total height or thickness of the test slide is required to be no more than 1.17 millimeters, then it is envisioned to form the four components of this particular embodiment of the hematology test slide 2, as follows: the thickness of the top housing member 6 within the recess 32 would have a maximum thickness of 0.30 millimeters; the bottom cover slip 12 would have a maximum thickness of 0.19 millimeters; the base plate 16 would have a recommended maximum thickness of 0.25 millimeters; and any air gap between the bottom cover slip 12 and the base plate 16 would have a maximum thickness of 0.03 millimeters. With such dimensions, a deeper maximum sample holding cell of 0.40 millimeters would be provided with the four-component version of the hematology test slide 2 shown in FIG. 22 than that resulting from the six-component design of the hematology test slide 2 shown in FIGS. 1-21 of the drawings. Another advantage would be, of course, a lower parts count and an expected lower cost to manufacture the slide 2.

With such a four-component embodiment, if the bottom surface of the base plate 16 is recessed inwardly from the bottom surface 34 of the top housing member 6, then the top housing member 6 and the cell depth set the distance from the top surface of the bottom cover slip 12 and the sapphire window of the optics module of the analyzer. If, however, the base plate 16 protrudes outwardly below the bottom surface 34 of the top housing member 6, then the distance from the top surface of the bottom cover slip 12 and the sapphire window of the analyzer's optics module would also include the thickness of the base plate 16. The base plate 16 may be attached to the top housing member 6 by solvent bonding, ultrasonic bonding or an adhesive that contributes minimal thickness to the overall height of the hematology test slide 2 or, in the five-component version, by the base gasket 14, preferably formed as a very thin transfer tape. In such an embodiment of the hematology test slide 2, where the top housing member 6 functions as the top cover slip 8, planarity in molding the components and the finish of the bottom surface 34 of the top housing member 6 within the recess 32 are important, as well as insuring that the bottom cover slip 12 is arranged within the top housing member 6 so that it will be parallel to the sapphire window of the analyzer's optics module.

In the five-component version of the hematology test slide, which includes the base gasket 14, it would be preferred if the base gasket 14 is formed with a maximum thickness of 0.03 millimeters, taking the place of the projected air gap between the bottom cover slip 12 and the base plate 16 in the four-component embodiment of the slide 2 described previously. The other components of the hematology test slide 2, that is, the maximum thicknesses of the top housing member 6 within the recess 32, the bottom cover slip 12 and the base plate 16 would be the same as those maximum thicknesses designated for the four-component version of the hematology test slide 2 to also arrive at a maximum total slide height of 1.17 millimeters. Then, such a five-component embodiment of the hematology test slide 2 would also provide a deeper maximum sample holding cell of up to 0.40 millimeters, that is, the same as that of the four-component version of the slide 2. Again, with the five-component embodiment of the hematology test slide 2, molding planarity of the components and a smooth finish in the recessed bottom surface 34 of the top housing member 6 should be maintained.

With the six-component embodiment of the hematology test slide 2 described previously and shown in FIGS. 1-21 of the drawings, and to achieve a maximum total slide height, or thickness, of 1.17 millimeters, the maximum thicknesses of the components of such a slide 2 should be the following: the top housing member 6 within the recess 32 should be no more than 0.30 millimeters; the bottom cover slip 12 should be no more than 0.18 millimeters; the top cover slip 8 should be no more than 0.18 millimeters; the base plate 16 should be no more than 0.25 millimeters; the base gasket 14 (e.g., a transfer tape) should be about 0.03 millimeters and any air gap between the bottom cover slip 12 and the base plate 16 should be about 0.03 millimeters. The maximum depth of the sample holding cell provided between the top cover slip 8 and the bottom cover slip 12 for this six-component version of the hematology test slide 2 having an overall slide thickness of 1.17 millimeters could be as much as 0.20 millimeters.

The hematology test slide 2 of the present invention having the same or similar outer dimensions of the chemical reagent test slide and the immunoassay test slide described previously allows the hematology slide 2 to be used in a single analyzer such that the analyzer has the capability to run clinical chemistry, electrolyte, immunoassay and hematology tests on a single whole blood sample in an efficient and automated fashion.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A hematology test slide, which comprises:
    a slide housing, the slide housing having a top housing member and a bottom housing member joined to the top housing member, the top and bottom housing members defining a cavity;
    a bottom cover slip; and
    a spacer interposed between the top housing member and the bottom cover slip, the spacer having a closed end portion and an open end portion, the open end portion being defined by a pair of spaced apart legs extending from the closed end portion, the closed end portion interiorly defining a sample deposit area, and the pair of spaced apart legs of the open end portion defining between the legs an optical read area, the bottom cover slip and the spacer being situated within the cavity of the slide housing;
    wherein the optical read area of the spacer is covered by the top housing member and the bottom cover slip;
    wherein the bottom housing member includes a base plate which is planar in form, the base plate being affixed to the top housing member to encapsulate within the cavity of the slide housing the spacer, the bottom cover slip and any fluid sample residing in the optical read area of the spacer;
    wherein the base plate includes an optical read opening formed through the thickness thereof, the optical read opening in the base plate being situated in alignment with the optical read area of the spacer;
    wherein the top housing member of the slide housing includes a sample deposit opening formed through the thickness thereof, the sample deposit opening being situated in alignment and in fluid communication with the sample deposit area of the spacer and for receiving through the sample deposit opening a fluid sample; and
    wherein the optical read opening formed in the base plate is offset from the sample deposit opening formed in the top housing member so as to be in non-alignment with the sample deposit opening.

2. A hematology test slide as defined by claim 1, wherein the closed end portion of the spacer includes a curved, semi-circular section; and
    wherein the legs of the open end portion of the spacer are straight members parallelly disposed to one another and which extend from the curved, semi-circular section of the closed end portion of the spacer.

3. A hematology test slide as defined by claim 1, wherein the spacer has a top surface and an opposite bottom surface;
    wherein each of the top housing member and the bottom cover slip has a top surface and an opposite bottom surface; and
    wherein at least a portion of the top surface of the spacer is in contact with the bottom surface of the top housing member, and the bottom surface of the spacer is in contact with the top surface of the bottom cover slip.

4. A hematology test slide as defined by claim 3, wherein at least a portion of the top surface of the spacer which is in contact with the bottom surface of the top housing member is adhesively joined to the bottom surface of the top housing member; and
    wherein the bottom surface of the spacer is adhesively joined to the top surface of the bottom cover slip.

5. A hematology test slide as defined by claim 4, wherein the spacer is formed from a double-sided adhesive tape.

6. A hematology test slide as defined by claim 5, wherein the double-sided adhesive tape from which the spacer is formed is a transfer tape.

7. A hematology test slide as defined by claim 3, wherein the bottom surface of the top housing member and the top surface of the bottom cover slip are spaced apart from each other at the optical read area a predetermined distance; and
    wherein the spacer has a specific thickness which defines the predetermined distance which the bottom surface of the top housing member is spaced from the top surface of the bottom cover slip over at least a portion of the spacer situated at the optical read area.

8. A hematology test slide as defined by claim 7, wherein the thickness of the spacer over the at least portion thereof situated at the optical read area is between about 3 microns and about 5 microns.

9. A hematology test slide as defined by claim 7, wherein the thickness of the spacer over the at least portion thereof situated at the optical read area is between about 5 microns and about 50 microns.

10. A hematology test slide as defined by claim 7, wherein the thickness of the spacer over the at least portion thereof situated at the optical read area is between about 25 microns and about 250 microns.

11. A hematology test slide as defined by claim 7, wherein the thickness of the spacer over the at least portion thereof situated at the optical read area is between about 25 microns and about 50 microns.

12. A hematology test slide as defined by claim 1, wherein the top housing member and the bottom cover slip are spaced apart from each other at the optical read area a predetermined distance to define a fluid holding cell having a measurable volume between the top housing member and the bottom cover slip situated at the optical read area.

13. A hematology test slide as defined by claim 1, wherein the slide housing is generally trapezoidal in overall shape, the housing including a front portion, a rear portion situated opposite the front portion, a first side portion and a second side portion situated opposite the first side portion;
wherein the front and rear portions are generally parallel to each other and the rear portion is longer than the front portion; and
wherein the first and second side portions extend between the front and rear portions in a mutually non-parallel direction.

14. A hematology test slide as defined by claim 1, wherein the top housing member of the slide housing has a planar structure and includes a top side and an opposite bottom side; and
wherein the bottom side of the top housing member has formed therein a recess which at least partially defines the cavity of the slide housing for receiving the spacer and the bottom cover slip.

15. A hematology test slide as defined by claim 1, which further comprises:
a base gasket, the base gasket being interposed between the bottom cover slip and the base plate.

16. A hematology test slide as defined by claim 15, wherein the base gasket is adhesively joined to the bottom cover slip and the base plate.

17. A hematology test slide as defined by claim 16, wherein the base gasket is formed from a double-sided adhesive tape to adhere the base plate to the bottom cover slip.

18. A hematology test slide as defined by claim 17, wherein the base gasket further adheres the base plate to the top housing member.

19. A hematology test slide as defined by claim 16, wherein the base gasket is a double-sided adhesive transfer tape.

20. A hematology test slide as defined by claim 1, wherein the top housing member of the slide housing is substantially opaque over at least a portion thereof situated in alignment with the optical read area of the spacer to serve as a backdrop for optical measurements conducted on a fluid sample residing within the optical read area.

21. A hematology test slide as defined by claim 1, wherein each of the top housing member and the bottom cover slip is formed from a hydrophilic material.

22. A hematology test slide as defined by claim 1, wherein at least the bottom cover slip is formed from a light transmissive material.

23. A hematology test slide as defined by claim 1, wherein at least the bottom cover slip is formed from glass.

24. A hematology test slide as defined by claim 1, wherein at least the bottom cover slip has a thickness of between about 160 microns and about 190 microns.

* * * * *